United States Patent [19]
Anantanarayan et al.

[11] Patent Number: 5,932,576
[45] Date of Patent: Aug. 3, 1999

[54] 3(5)-HETEROARYL SUBSTITUTED PYRAZOLES AS P38 KINASE INHIBITORS

[75] Inventors: Ashok Anantanarayan, Hainesville; Michael Clare, Skokie; Lifeng Geng, Skokie; Gunnar J. Hanson, Skokie; Richard A. Partis, Evanston; Michael A. Stealey, Libertyville; Richard M. Weier, Lake Bluff, all of Ill.

[73] Assignee: G. D. Searle & Company, Chicago, Ill.

[21] Appl. No.: 09/083,923

[22] Filed: May 22, 1998

Related U.S. Application Data

[60] Provisional application No. 60/047,535, May 22, 1997.

[51] Int. Cl.$^6$ ............. A61K 31/44; A61K 31/445; A61K 31/535; C07D 401/04; C07D 403/04; C07D 413/04

[52] U.S. Cl. ................... 514/235.5; 514/237.2; 514/255; 514/318; 514/341; 544/124; 546/193; 546/275.4

[58] Field of Search ................ 546/193, 275.4; 544/124; 514/341, 318, 255, 237.2, 235.5

[56] References Cited

U.S. PATENT DOCUMENTS

| | | | |
|---|---|---|---|
| 3,254,093 | 5/1966 | Huisgen et al. | 260/295 |
| 3,984,431 | 10/1976 | Guérémy et al. | 260/310 |
| 4,000,281 | 12/1976 | Beiler et al. | 424/263 |
| 5,051,518 | 9/1991 | Murray et al. | 546/274.7 |
| 5,134,142 | 7/1992 | Matsuo et al. | 514/255 |
| 5,559,137 | 9/1996 | Adams et al. | 514/341 |
| 5,589,439 | 12/1996 | Goto et al. | 504/261 |

FOREIGN PATENT DOCUMENTS

| | | |
|---|---|---|
| 0 115 640 A2 | 12/1983 | European Pat. Off. . |
| 0 418 845 | 3/1991 | European Pat. Off. . |
| 0 515 041 A2 | 11/1992 | European Pat. Off. . |
| 0 531 901 A2 | 3/1993 | European Pat. Off. . |
| 4-145081 | 5/1992 | Japan . |
| 5-17470 | 1/1993 | Japan . |
| 5-345772 | 12/1993 | Japan . |
| 8-183787 | 7/1996 | Japan . |
| WO 83/00330 | 2/1983 | WIPO . |
| WO 92/19615 | 11/1992 | WIPO . |
| WO 95/06036 | 3/1995 | WIPO . |
| WO 96/03385 A1 | 2/1996 | WIPO . |
| WO 96/21452 | 7/1996 | WIPO . |
| WO 97/01551 | 1/1997 | WIPO . |

OTHER PUBLICATIONS

Sep. 25, 1998 PCT International Search Report (PCT/US98/10807).

Moerck R E et al, "Pyrazole addition to 2H–azirines. Structure of purported 2:1 adducts of 2H–azirines with sym–tetrazines" J. Chem. Soc., Chem. Commun., No. 19, 1974. pp. 782–783.

Dannhardt G et al, "Transformations of pyrrolidine enaminones yielding (.omega.–aminopropyl)pyrazoles", Arch. Pharm., vol. 321, No. 1, 1988, pp. 17–19.

*Primary Examiner*—Floyd D. Higel
*Attorney, Agent, or Firm*—Joseph W. Bulock; Alan L. Scrivner

[57] ABSTRACT

A class of pyrazole derivatives is described for use in treating p38 kinase mediated disorders. Compounds of particular interest are defined by Formula I

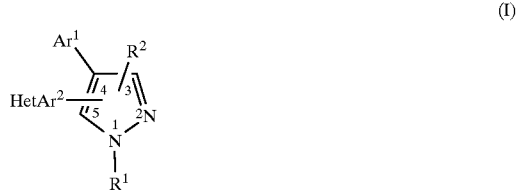

(I)

50 Claims, No Drawings

3(5)-HETEROARYL SUBSTITUTED PYRAZOLES AS P38 KINASE INHIBITORS

CROSS-REFERENCE TO RELATED APPLICATION

This application claims priority from U.S. Provisional Application Serial No. 60/047,535 filed May 22, 1997.

FIELD OF THE INVENTION

This invention relates to a novel group of pyrazole compounds, compositions and methods for treating p38 kinase mediated disorders.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. The p38 MAP kinase group is a MAP family of various isoforms, including p38α, p39β and p38γ, and is responsible for phosphorylating and activating transcription factors (e.g. ATF2, CHOP and MEF2C) as well as other kinases (e.g. MAPKAP-2 and MAPKAP-3). The p38 isoforms are activated by bacterial lipopolysaccharide, physical and chemical stress and by pro-inflammatory cytokines, including tumor necrosis factor (TNF-α) and interleukin-1 (IL-1). The products of the p38 phosphorylation mediate the production of inflammatory cytokines, including TNF and IL-1, and cyclooxygenase-2.

TNF-α is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

IL-8 is another pro-inflammatory cytokine, which is produced by mononuclear cells, fibroblasts, endothelial cells, and keratinocytes, and is associated with conditions including inflammation.

IL-1 is produced by activated monocytes and macrophages and is involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

Various pyrazoles have previously been described. U.S. Pat. No. 4,000,281, to Beiler and Binon, describes 4,5-aryl, heteroaryl substituted pyrazoles with antiviral activity against both RNA and DNA viruses such as myxoviruses, adenoviruses, rhinoviruses, and various viruses of the herpes group. WO 92/19615, published Nov. 12, 1992, describes pyrazoles as novel fungicides. U.S. Pat. No. 3,984,431, to Cueremy and Renault, describes derivatives of pyrazole-5-acetic acid as having antiinflammatory activity. Specifically, [1-isobutyl-3,4-diphenyl-1H-pyrazol-5-yl]acetic acid is described. U.S. Pat. No. 3,245,093 to Hinsgen et al, describes a process for preparing pyrazoles. WO 83/00330, published Feb. 3, 1983, describes new process for the preparation of diphenyl-3,4-methyl-5-pyrazole derivatives. WO 95/06036, published for preparing pyrazole and its derivatives. U.S. Pat. No. 5,589,439, to T. Goto, et al., describes tetrazole derivatives and their use as herbicides. EP 515041 describes pyrimidyl substituted pyrazole derivatives as novel agricultural fungicides. Japanese Patent 4,145,081 describes pyrazolecarboxylic acid derivatives as herbicides used in paddy fields, dry fields as well as non-agricultural areas. Japanese Patent 5,345,772 describes novel pyrazole derivatives having potent inhibitory activity against acetylcholinesterase.

Pyrazoles have been described for use in the treatment of inflammation. Japanese Patent 5,017,470 describes synthesis of pyrazole derivatives as anti-inflammatory, anti-rheumatic, anti-bacterial and anti-viral drugs. EP 115640, published Dec. 30, 1983, describes 4-imidazolyl-pyrazole derivatives as inhibitors of thromboxane synthesis. 3-(4-Isopropyl-1-methylcyclohex-1-yl)-4-(imidazol-1-yl)-1H-pyrazole is specifically described. WO 97/01551, published Jan. 16, 1997, describes pyrazole compounds as adenosine antagonists. 4-(3-Oxo-2,3-dihydropyridazin-6-yl)-3-phenylpyrazole is specifically described. U.S. Pat. No. 5,134,142, to Matsuo et al. describes 1,5-diaryl pyrazoles as having anti-inflammatory activity.

U.S. Pat. No. 5,559,137 to Adams et al, describes novel pyrazoles (1,3,4,-substituted) as inhibitors of cytokines used in the treatment of cytokine diseases. Specifically, 3-(4-fluorophenyl)-1-(4-methylsulfinylphenyl)-4-(4-pyridyl)-5H-pyrazole is described. WO 96/03385, published Feb. 8, 1996, describes 3,4-substituted pyrazoles, as having anti-inflammatory activity. Specifically, 4-[1-ethyl-4-(4-pyridyl)-5-trifluoromethyl-1H-pyrazol-3-yl]benzenesulfonamide is described.

The invention's pyrazolyl compounds are found to show usefulness as p38 kinase inhibitors.

DESCRIPTION OF THE INVENTION

A class of substituted pyrazolyl compounds useful in treating p38 mediated disorders is defined by Formula I:

wherein $R^1$ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and $R^2$ is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are optionally substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and $Ar^1$ is aryl optionally substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and $HetAr^2$ is pyridinyl, pyrimidinyl or quinolinyl optionally substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

Compounds of Formula I would be useful for, but not limited to, the treatment of any disorder or disease state in a human, or other mammal, which is excacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpesvirus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention also would be useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemaginomas, including invantile hemaginomas, angiofibroma of the nasopharynx and avascular necrosis of bone; diabetic nephropathy and cardiomyopathy; and disorders of the female reproductive system such as endometriosis. The compounds of the invention may also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

A preferred class of compounds consists of those compounds of Formula I wherein $R^1$ is selected from hydrido, lower alkyl, lower cycloalkyl, lower cycloalkylalkylene, lower haloalkyl, lower hydroxyalkyl, lower alkenyl, lower alkynyl, lower heterocyclyl, lower aralkyl, lower alkoxyalkyl, lower mercaptoalkyl, lower alkylthioalkylene, amino, lower alkylamino, lower arylamino, lower aminoalkyl, lower alkylaminoalkylene, lower heterocyclylalkylene, lower aminocarbonylalkylene, and lower alkylaminocarbonylalkylene; and $R^2$ is selected from hydrido, lower alkyl, lower alkenyl, lower alkynyl, lower haloalkyl, lower heterocyclyl, lower heterocyclylalkylene, amino, lower alkylamino, lower alkynylamino, lower aminoalkyl, lower alkylthio, lower carboxy, lower alkoxycarbonyl, lower carboxyalkyl, lower aminocarbonylamino, lower alkylaminocarbonylamino, lower alkylsulfonyl, lower aminosulfonyl, lower alkylsulfonylamino, lower aminosulfonylamino, and lower alkylaminosulfonylamino, wherein the heterocyclyl and heterocyclylalkyl groups are optionally substituted with one or more radicals independently selected from lower alkylthio, lower alkylsulfonyl, lower alkylsulfinyl, halo, lower alkyl, lower alkoxy, aryloxy, lower heterocyclyl, lower haloalkyl, amino, and cyano; and $Ar^1$ is selected from phenyl, biphenyl, and naphthyl, wherein $Ar^1$ is optionally substituted with one or more radicals independently selected from lower alkylthio, lower alkylsulfonyl, aminosulfonyl, halo, lower alkyl, lower alkenyl, lower alkynyl, lower alkylsulfinyl, cyano, lower alkoxycarbonyl, aminocarbonyl, formyl, lower alkylcarbonylamino, lower haloalkyl, lower alkoxy, lower alkenyloxy, lower alkyldioxy, amino, lower alkylamino, lower aminoalkyl, arylamino, nitro, and halosulfonyl; and $HetAr^2$ is pyridinyl or pyrimidinyl optionally substituted with one or more radicals independently selected from lower alkylthio, lower alkylsulfonyl, lower alkylsulfinyl, halo, lower alkyl, lower heterocyclyl, lower alkoxy, lower aralkoxy, lower haloalkyl, amino, cyano, lower aralkyl, lower alkylamino, lower cycloalkylamino, lower arylamino, lower alkynylamino, and lower aralkylamino; or a pharmaceutically-acceptable salt or tautomer thereof.

A class of compounds of particularly interest consists of these compounds of Formula I wherein $R^1$ is selected from hydrido, methyl, ethyl, isopropyl, tert-butyl, isobutyl, trichloroethyl, pentafluoroethyl, heptafluoropropyl, difluoroethyl, difluoropropyl, dichloroethyl, dichloropropyl, vinyl, allyl, ethynyl, propargyl, morpholinyl, piperidinyl, piperazinyl, benzyl, phenylethyl, morpholinomethyl, morpholinoethyl, pyrrolidinylmethyl, piperazinylmethyl, piperidinylmethyl, pyridinylmethyl, thienylmethyl, methoxymethyl, ethoxymethyl, amino, methylamino, dimethylamino, phenylamino, methylaminomethyl, dimethylaminomethyl, methylaminoethyl, dimethylaminoethyl, cyclopropyl, cyclopentyl, cyclohexyl, cyclohexylmethyl, hydroxymethyl, hydroxyethyl, methylthio, and methylthiomethyl; and $R^2$ is selected from hydrido, methyl, ethyl, propyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, amino, N-methylamino, N,N-dimethylamino, ethynylamino, propargylamino, piperidinyl, piperazinyl, morpholinomethyl, pyrrolidinylmethyl, piperazinylmethyl, piperidinylmethyl, pyridinylmethyl, thienylmethyl, thiazolylmethyl, oxazolylmethyl, pyrimidinylmethyl, quinolylmethyl, isoquinolinylmethyl, imidazolylmethyl, benzimidazolylmethyl, furylmethyl, pyrazinylmethyl, aminocarbonylamino, methylaminocarbonylamino, dimethylaminocarbonylamino, ethylaminocarbonylamino, diethylaminocarbonylamino, methylsulfonylamino, ethylsulfonylamino, aminosulfonylamino, methylaminosulfonylamino, dimethylaminosulfonylamino, ethylaminosulfonylamino, and diethylaminosulfonylamino; and $Ar^1$ is selected from phenyl, biphenyl, and naphthyl, wherein $Ar^1$ is optionally substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, allyl, vinyl, ethynyl, propargyl, methoxy, ethoxy, propyloxy, n-butoxy, amino, methylamino, ethylamino, dimethylamino, diethylamino, aminomethyl, aminoethyl, N-methyl, N-phenylamino, phenylamino, diphenylamino, nitro, and chlorosulfonyl; and $HetAr^2$ is selected from pyridinyl and pyrimidinyl, wherein $HetAr^2$ is optionally substituted with one or more radicals independently selected from methylthio, methylsulfinyl, methylsulfonyl, fluoro, chloro, bromo, methyl, ethyl, isopropyl, tert-butyl, isobutyl, methoxyl, ethoxyl, phenoxyl, benzoxyl, phenethyl, trifluoromethyl, fluoromethyl, difluoromethyl, amino, benzylamino, propargylamino, cyclopropylamino, cyclobutylamino, cyclopentylamino, and cyano; or a pharmaceutically-acceptable salt or tautomer thereof.

A class of compounds of specific interest consists of those compounds of Formula I wherein $R^1$ is hydrido, methyl, ethyl, hydroxyethyl, propargyl, dimethylaminoethyl or morpholinoethyl; and $R^2$ is selected from hydrido, methyl, ethyl, amino, aminocarbonylamino, methylaminocarbonylamino, methylsulfonylamino, aminosulfonylamino, and methylaminosulfonylamino; and $Ar^1$ is phenyl optionally substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, methoxy, ethoxy, propyloxy, n-butoxy, amino, methylamino, ethylamino, dimethylamino, diethylamino, aminomethyl, aminoethyl, N-methyl, N-phenylamino, phenylamino, diphenylamino, nitro, and chlorosulfonyl; and $HetAr^2$ is optionally substituted with one or more radicals independently selected from methylthio, methylsulfinyl, methylsulfonyl, fluoro, chloro, bromo, methyl, ethyl, isopropyl, tert-butyl, isobutyl, methoxyl, ethoxyl, phenoxyl, benzoxyl, trifluoromethyl, fluoromethyl, difluoromethyl, amino, propargylamino, and cyano; or a pharmaceutically-acceptable salt or a tautomer thereof.

A class of compounds of very specific interest consists of those compounds of Formula I wherein $R^1$ is hydrido or methyl; and $R^2$ is hydrido or methyl; and $Ar^1$ is phenyl which is optionally substituted with one or more radicals independently selected fluoro, chloro, methyl, ethyl, trifluoromethyl, methoxy, ethoxy, dimethylamino, and nitro; and $HetAr^2$ is optionally substituted with one or more radicals independently selected from methyl, chloro, fluoro, and trifluoromethyl; or a pharmaceutically-acceptable salt or tautomer thereof.

A family of specific compounds of particular interest within Formula I consists of compounds, and tautomers and pharmaceutically-acceptable salts thereof, as follows:

4-(3-methyl-4-phenyl-1H-pyrazol-5-yl)pyridine;
4-(4-fluorophenyl)-5-(4-pyridinyl)-1H-pyrazol-3-amine;
N-[4(4-fluorophenyl)-5-(4-pyridinyl)-1H-pyrazol-3-yl] methanesulfonamide;
N-[4-(4-fluorophenyl)-5-(4-pyridinyl)-1H-pyrazol-3-yl]-N'-methylsulfamide;
[4-(4-fluorophenyl)-5-(4-pyridinyl)-1H-pyrazol-3-yl]urea;
[4-(4-fluorophenyl)-5-(4-pyridinyl)-1H-pyrazol-3-yl] sulfamide;

4-(4-chlorophenyl)-1-methyl-3-(4-pyridinyl)-1H-pyrazol-5-amine;

N-[4-(4-fluorophenyl)-5-(4-pyridinyl)-1H-pyrazol-3-yl]-N'-methylurea;

4-[4-(4-fluorophenyl)-1H-pyrazol-3-yl]pyridine;

4-[4-(4-fluorophenyl)-1-methyl-1H-pyrazol-3-yl]pyridine;

4-(4-fluorophenyl)-3-(4-pyridinyl)-1H-pyrazole-1-ethanol;

4-(4-fluorophenyl)-N,N-dimethyl-3-(4-pyridinyl)-1H-pyrazole-1-ethanamine;

4-[2-[4-(4-fluorophenyl)-3-(4-pyridinyl)-1H-pyrazol-1-yl]ethyl]morpholine;

4-[4-(4-chlorophenyl)-1H-pyrazol-3-yl]pyridine;

4-(4-phenyl-1H-pyrazol-5-yl)pyridine;

1-methyl-4-[2-[4-(4-fluorophenyl)-3-(4-pyridinyl)-1H-pyrazol-1-yl]]piperidine; and 1-methyl-4-[2-[4-(4-fluorophenyl)-5-(4-pyridinyl)-1H-pyrazol-1-yl]piperidine.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl", "hydroxyalkyl", "mercaptoalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations. The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about six carbon atoms. Examples of alkynyl radicals include propargyl, 1-propynyl, 2-propynyl, 1-butyne, 2-butenyl and 1-pentynyl. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkylalkylene" embraces alkyl radicals substituted with a cycloalkyl radical. More preferred cycloalkylalkylene radicals are "lower cycloalkylalkylene" which embrace lower alkyl radicals substituted with a lower cycloalkyl radical as defined above. Examples of such radicals include cyclopropylmethyl, cyclobutylmethyl, cyclopentylmethyl and cyclohexylmethyl. The term "cycloalkenyl" embraces partially unsaturated carbocyclic radicals having three to twelve carbon atoms and one or two double bonds but not necessarily conjugated ("cycloalkyldienyl"). More preferred cycloalkenyl radicals are "lower cycloalkenyl" radicals having four to about eight carbon atoms. Examples of such radicals include cyclobutenyl, cyclopentenyl and cyclohexenyl. The term "cycloalkenylalkylene" embraces alkyl radicals substituted with a cycloalkenyl radical. More preferred cycloalkenylalkylene radicals are "lower cycloalkenylalkylene" which embrace lower alkyl radicals substituted with a lower cycloalkenyl radical, as defined above. Examples of such radicals include cyclobutenylmethyl, cyclopentenylmethyl and cyclohexenylmethyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms, any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical to form, for example, monoalkoxyalkyl and dialkoxyalkyl radicals. The "alkoxy" radicals may be further substituted with one or more halo atoms, such as fluoro, chloro or bromo, to provide "haloalkoxy" radicals.

The term "aryl", alone or in combination, means a carbocyclic aromatic system containing one, two or three rings wherein such rings may be attached together in a pendent manner or may be fused. More preferred aryl are 6–12 membered aryl radicals. Examples of such radicals include phenyl, naphthyl, tetrahydronaphthyl, indane and biphenyl. Aryl moieties may also be substituted at a substitutable position with one or more substituents selected independently from, for example, halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl, alkoxyalkyl, alkylaminoalkyl, carboxyalkyl, alkoxycarbonylalkyl, aminocarbonylalkyl, aralkoxy, hydroxyl, acyl, carboxy, aminocarbonyl, and aralkoxycarbonyl. The term "alkyldioxy" encompasses an alkyldioxy bridge, such as a methylenedioxy bridge, between two carbon ring atoms of an aryl moiety.

The term "heterocyclyl" embraces saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term "heteroaryl" also embraces radicals where heterocyclyl radicals are fused with aryl radicals. Examples of such fused bicyclic radicals include benzofuran, benzothiophene, and the like. Said heterocyclyl group may have 1 to 3 substituents such as alkyl, hydroxyl, halo, alkoxy, oxo, amino and alkylamino. The term "heterocyclylalkylene" embraces heterocyclyl-substituted alkyl radicals. More preferred heterocyclylalkylene radicals are "lower heterocyclylalkylene" radicals having one to six carbon atoms and a heterocyclyl radical.

The term "alkylthiol" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkylene" embraces radicals containing an alkylthio radical attached through the divalent sulfur atom to an alkyl radical of one to about ten carbon atoms. More preferred alkylthioalkylene radicals are "lower alkylthioalkylene" radicals having alkyl radicals of one to six carbon atoms. Examples of such lower alkylthioalkylene radicals include methylthiomethyl. The term "alkylsulfinyl" embraces radicals containing a linear or branched alkyl radical, of one to about ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as "alkylsulfonyl", or "halosulfonyl" denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The term "halosulfonyl" embraces halo radicals attached to a sulfonyl radical. Examples of such halosulfonyl radicals include chlorosulfonyl and bromosulfonyl. The terms "sulfamyl", "aminosulfonyl" and "sulfonamidyl" denote NH$_2$O$_2$S—.

The term "carbonyl", whether used alone or with other terms, such as "alkoxycarbonyl", denotes —(C=O)—. The terms "carboxy" or "carboxyl", whether used alone or with other terms, such as "carboxyalkyl", denotes —CO$_2$H. The term "carboxyalkyl", embraces alkyl radicals substituted with a carboxy radical. More preferred are "lower carboxyalkyl" radicals which embrace carboxy-substituted lower alkyl radicals, as defined above. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having one to six carbons. Examples of such lower alkoxycarbonyl (ester) radicals include methoxycarbonyl, ethoxycarbonyl, propoxycarbonyl, butoxycarbonyl and hexyloxycarbonyl. The term "alkoxycarbonylalkylene" embraces alkyl radicals substituted with an alkoxycarbonyl radical as defined above. More preferred are "lower alkoxycarbonylalkylene" radicals with alkyl portions having one to six carbons. Examples of such lower alkoxycarbonylalkylene radicals include methoxycarbonylmethylene, ethoxycarbonylmethylene, methoxycarbonylethylene and ethoxycarbonylethylene. The term "alkylcarbonyl", includes radicals having alkyl radicals attached to a carbonyl radical. Examples of such radicals include methylcarbonyl, ethylcarbonyl, propylcarbonyl, butylcarbonyl, and pentylcarbonyl. The term "aralkyl" embraces aryl-substituted alkyl radicals. Preferred aralkyl radicals are "lower aralkyl", having lower alkyl groups substituted with one or more aryl groups. Examples of such groups include benzyl, diphenylmethyl, triphenylmethyl, phenylethyl, and diphenylethyl. The aryl in said aralkyl may be additionally substituted with halo, alkyl, alkoxy, haloalkyl and haloalkoxy. The terms benzyl and phenylmethyl are interchangeable. The term "heterocyclylalkylene" embraces saturated, partially unsaturated and unsaturated heterocyclyl-substituted alkyl radicals such as pyrrolidinylmethyl, pyridylmethyl, quinolylmethyl, thienylmethyl, furylethyl, and quinolylethyl. The heteroaryl in heteroaralkyl (unsaturated heterocyclyl-substituted alkyl radicals) may be additionally substituted with halo, alkyl, alkoxy, haloalkyl and haloalkoxy. The term "aryloxy" embraces aryl radicals attached through an oxygen atom to other radicals. The term "aralkoxy" embraces aralkyl radicals attached through an oxygen atom to other radicals.

The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which are substituted with one or two alkyl radicals. Preferred are "lower alkylamino" radicals having alkyl portions having one to six carbon atoms. Suitable lower alkylamino may be monosubstituted N-alkylamino or disubstituted N,N-alkylamino, such as N-methylamino, N-ethylamino, N,N-dimethylamino, N,N-diethylamino or the like. The term "arylamino" denotes amino groups which are substituted with one or two aryl radicals, such as N-phenylamino. The "arylamino" radicals may be further substituted on the aryl ring portion of the radical. The term "aminocarbonyl" denotes an amide group of the formula —C(=O)NH. The term "alkylaminocarbonyl" denotes an aminocarbonyl group which has been substituted with one or two alkyl radicals on the amino nitrogen atom. Preferred are "N-alkylaminocarbonyl" and "N,N-dialkylaminocarbonyl" radicals. More preferred are "lower N-alkylaminocarbonyl" and "lower N,N-dialkylaminocarbonyl" radicals with lower alkyl portions as defined above. The term "aminocarbonylamino" embraces radicals having one or more aminocarbonyl radicals attached to an amino radical. The term "alkylaminocarbonylamino" embraces radicals having one or more alkyl radicals attached to an aminocarbonylamino radical. Preferred are "lower alkylaminocarbonylamino" radicals with lower alkyl portions as defined above. The term "alkylcarbonylamino" embraces amino groups which are substituted with one or more alkylcarbonyl radicals. More preferred alkylcarbonylamino radicals are "lower alkylcarbonylamino" having lower alkylcarbonyl radicals as defined above attached to amino radicals. The term "alkylaminoalkylene" embraces radicals having one or more alkyl radicals attached to an aminoalkyl radical. The term "alkylsulfonylamino" embraces radicals having one or more alkylsulfonyl radicals attached to an amino radical. Preferred are "lower alkylsulfonylamino" radicals with lower alkyl portions as defined above. The term "aminosulfonylamino" embraces radicals having one or more aminosulfonyl radicals attached to an amino radical. The term "alkylaminosulfonylamino" embraces radicals having one or more alkyl radicals attached to an aminosulfonylamino radical. Preferred are "lower alkylaminosulfonylamino" radicals with lower alkyl portions as defined above.

The additional terms used to describe the substituents of the pyrazole ring and not specifically defined herein are defined in a similar manner to that illustrated in the above definitions. As above, more preferred substituents are those containing "lower" radicals. Unless otherwise defined to contrary, the term "lower" as used in this application means that each alkyl radical of a pyrazole ring substituent comprising one or more alkyl radicals has one to about six carbon atoms; each alkenyl radical of a pyrazole ring substituent comprising one or more alkenyl radicals has two to about six carbon atoms; each alkynyl radical of a pyrazole ring substituent comprising one or more alkynyl radicals has two to about six carbon atoms; each cycloalkyl or cycloalkenyl radical of a pyrazole ring substituent comprising one or more cycloalkyl and/or cycloalkenyl radicals is a 3 to 8 membered ring cycloalkyl or cycloalkenyl radical, respectively; each aryl radical of a pyrazole ring substituent comprising one or more aryl radicals is a monocyclic aryl radical; and each heterocyclyl radical of a pyrazole ring substituent comprising one or more heterocyclyl radicals is a 4-8 membered ring heterocyclyl.

The present invention comprises the tautomeric forms of compounds of Formula I. As illustrated below, the pyrazoles of Formula I and I' are magnetically and structurally equivalent because of the prototropic tautomeric nature of the hydrogen:

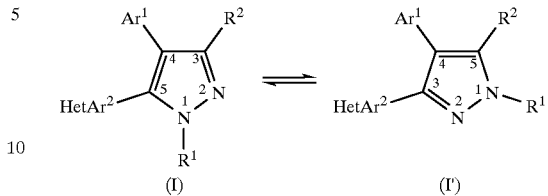

The present invention also comprises compounds of Formula I having one or more asymmetric carbons. It is known to those skilled in the art that those pyrazoles of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

The present invention comprises a pharmaceutical composition for the treatment of a TNF mediated disorder, a p38 kinase mediated disorder, inflammation, and/or arthritis, comprising a therapeutically-effective amount of a compound of Formula I, or a therapeutically-acceptable salt or tautomer thereof, in association with at least one pharmaceutically-acceptable carrier, adjuvant or diluent.

The present invention also comprises a therapeutic method of treating a TNF mediated disorder, a p38 kinase mediated disorder, inflammation and/or arthritis in a subject, the method comprising treating a subject having or susceptible to such disorder or condition with a therapeutically-effective amount of a compound of Formula I (I)

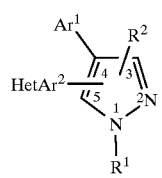

wherein $R^1$ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and $R^2$ is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are optionally substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and $Ar^1$ is aryl optionally substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr$^2$ is pyridinyl, pyrimidinyl or quinolinyl optionally substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acid. Suitable pharmaceutically-acceptable base addition salts of compounds of Formula I include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine. All of these salts may be prepared by conventional means form the corresponding compound of Formula I by reacting, for example, the appropriate acid or base with the compound of Formula I.

General Synthetic Procedures

The compounds of the invention can be synthesized according to the following procedures of Schemes I–VI wherein the R$^1$–R$^3$ substituents and Ar$^1$, HetAr$^2$ are as defined for Formula I, above, except where further noted.

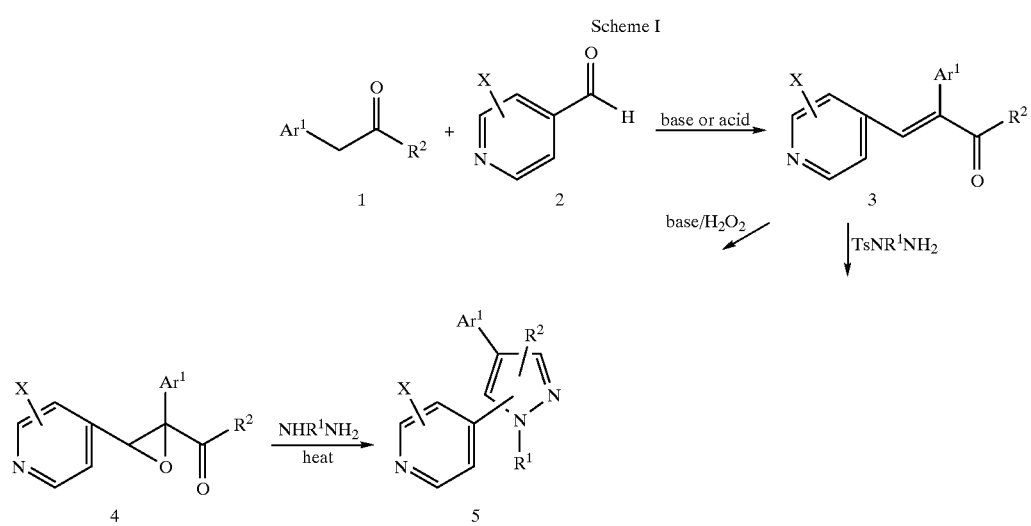

Scheme I shows the three step preparation of the pyrazole 5 of the present invention. In step 1, the reaction of arylmethyl derived ketone 1 with pyridine derived aldehyde 2 either in a solvent such as benzene or toluene in the presence of a base such as pyridine or in a mixture of acids such as acetic acid and hydrogen bromide gives the α,β-unsaturated ketone 3. In step 2, in the presence of base such as sodium hydroxide, α,β-unsaturated ketone 3 is converted to the corresponding epoxide 4 by the treatment with hydrogen peroxide solution at room temperature. In step 3, epoxide 4 is condensed with hydrazine in a suitable solvent such as ethanol at temperature ranging up to the boiling point to form pyrazole 5. Alternatively, pyrazole 5 can be prepared by treatment of 3 with tosyl hydrazide in the presence of an acid such as acetic acid at reflux.

Scheme II

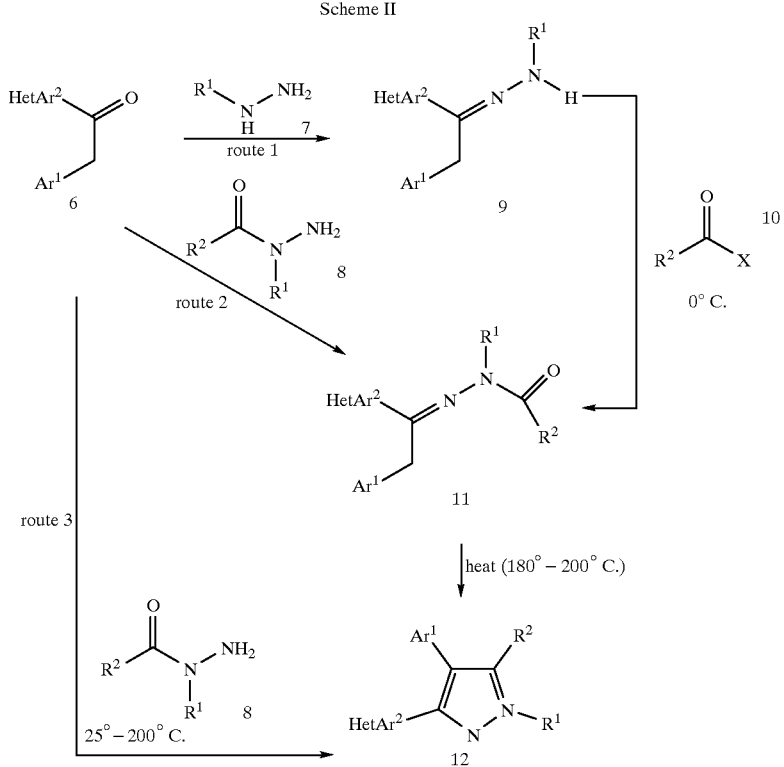

Scheme II shows the synthesis of pyrazole 12 containing a heteroaromatic ring by three routes. In Route 1, ketone 6 is condensed with hydrazine 7 to give substituted hydrazine 9, which is then reacted with acyl halide or anhydride 10 at low temperature to provide acyl hydrazone 11. Upon heating at temperature up to 200° C., hydrazone 11 is converted to pyrazole 12. In Route 2, acyl hydrazone 11 is formed directly by reaction of ketone 6 with acyl hydrazide 8 at room temperature. Acyl hydrazide 8 may be formed by reaction of hydrazine with a carboxylic acid ester. Heating 11 as above then provides pyrazole 12. In Route 3, ketone 6 is treated with acyl hydrazide 8 at from room temperature to ~200° C. to give pyrazole 12 directly. Alternatively, this condensation may be carried out in an acidic solvent, such as acetic acid, or in a solvent containing acetic acid.

Scheme III

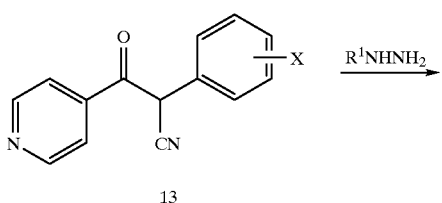

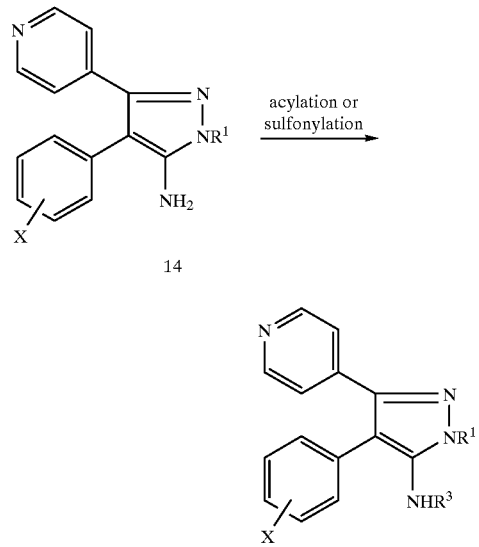

Cyanoketone 13 may be synthesized according to the procedure described by I. Lantos et al in *J. Org. Chem.*, volume 53, pp. 4223–4227 (1988) for the synthesis of the p-fluoro compound (X=p-F). This procedure, which is incorporated herein by reference, can be used to synthesize cyanoketones such as 13 wherein X is selected from, for example, halogen, alkyl and alkoxy. Cyanoketones such as 13 may be converted to pyrazoles 14 by reaction with a hydrazine in a suitable solvent, such as benzene or toluene.

A catalyst such as acetic acid may be employed. When hydrazine itself is employed, the ring nitrogen atoms of the pyrazole thus obtained bear no substituent except hydrogen on one of the ring nitrogen atoms. When a substituted hydrazine, such as methylhydrazine is employed, the product pyrazole 14 bears a substituent on the ring nitrogen atom adjacent to the aminated ring carbon atom, as shown in Scheme 1. The resultant aminopyrazole 14 may be acylated or sulfonylated to form substituted aminopyrazole 15 by treatment with a suitably activated carboxylic or sulfonic acid in a suitable solvent such as pyridine. Examples of a suitably activated carboxylic acid include acetic anhydride or benzoyl chloride. Examples of a suitably activated sulfonic acid include methanesulfonyl chloride, p-toluenesulfonyl chloride or sulfamyl chloride.

reacted with pyridine 17 in the presence of a base, such as an alkali metal alkoxide (preferably sodium methoxide), in a suitable solvent, such as tetrahydrofuran. Subsequent treatment with an acid, preferably a mineral acid such as hydrochloric acid, yields the desoxybenzoin 18. Desoxybenzoin 18 is then converted to ketone 19 by treatment with an excess of dimethylformamide dimethyl acetal. Ketone 19 is then reacted with hydrazine in a suitable solvent such as ethanol to yield a mixture of pyrazoles 20 and 21. In Scheme IV, $R^4$ represents one or more radicals independently selected from the optional substituents previously defined for $Ar^1$; and $R^5$ represents one or more radicals independently selected from the optional substituents previously defined for $HetAr^2$.-

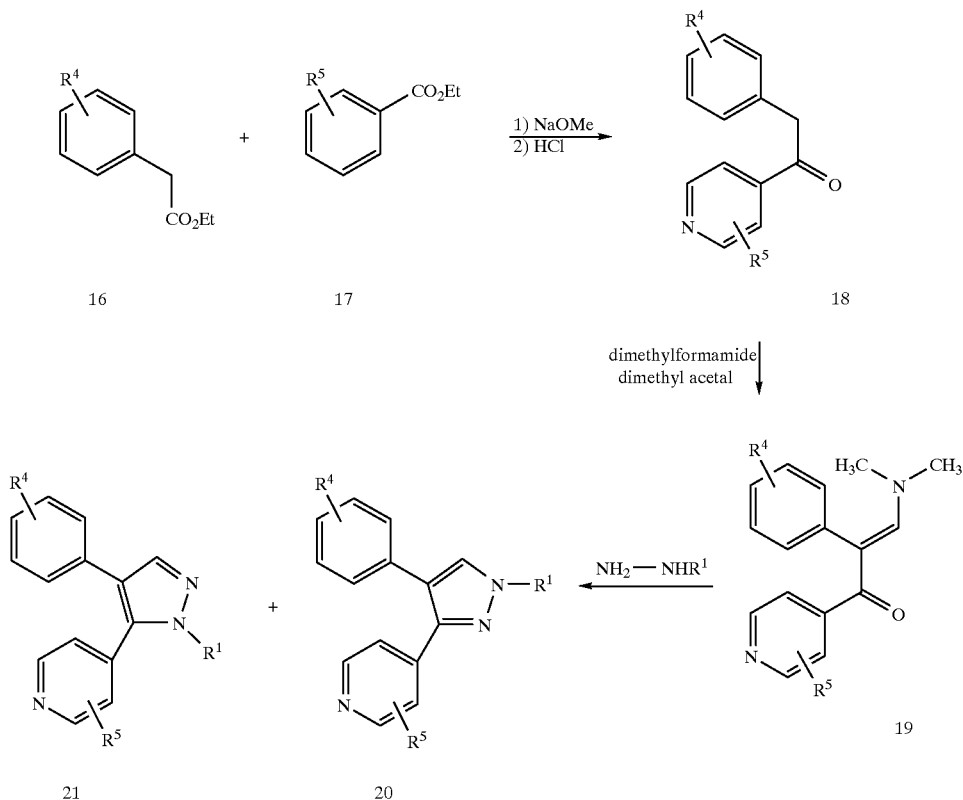

Scheme IV

Scheme IV illustrates the synthesis of 3-pyridyl-4-aryl-pyrazoles of the present invention. Benzoate 16 is first The 3-pyrimidinyl-4-aryl-pyrazoles of the present invention can be synthesized in the manner of Scheme IV by replacing pyridine 17 with the corresponding pyrimidine.

Scheme V

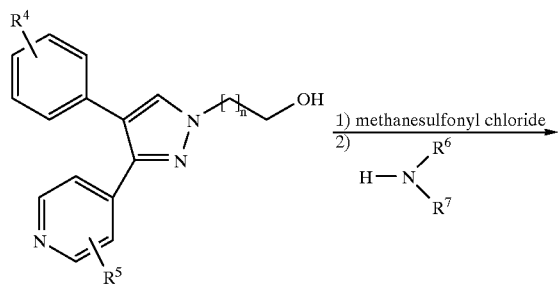

22

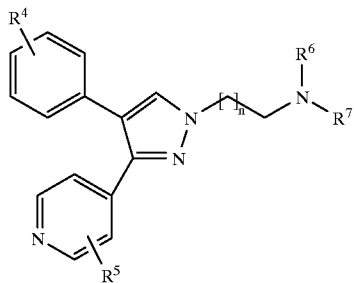

24

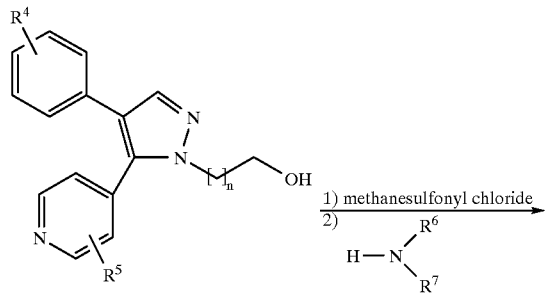

23

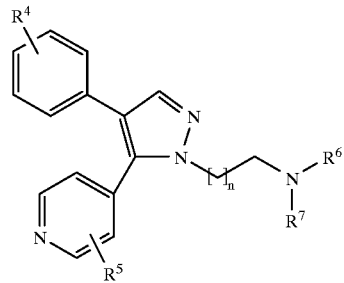

25

In Scheme V, hydroxyalkyl pyrazoles 22 and 23 are converted to sulfonate derivatives by reaction with an alkyl- or arylsulfonyl halide. These sulfonates are then reacted with ammonia or primary amines or secondary amines to give the corresponding 1-amino-pyrazoles 24 and 25, respectively. In Scheme V, n is 1, 2, 3, 4 or 5; $R_4$ and $R^5$ are as defined in Scheme IV; $R^6$ and $R_7$ are independently selected, for example, from hydrogen, alkyl and aryl, or together with the nitrogen atom to which they are attached form a 4-8 membered ring that may contain one or more additional heteroatoms selected from oxygen, nitrogen or sulfur.

Scheme VI

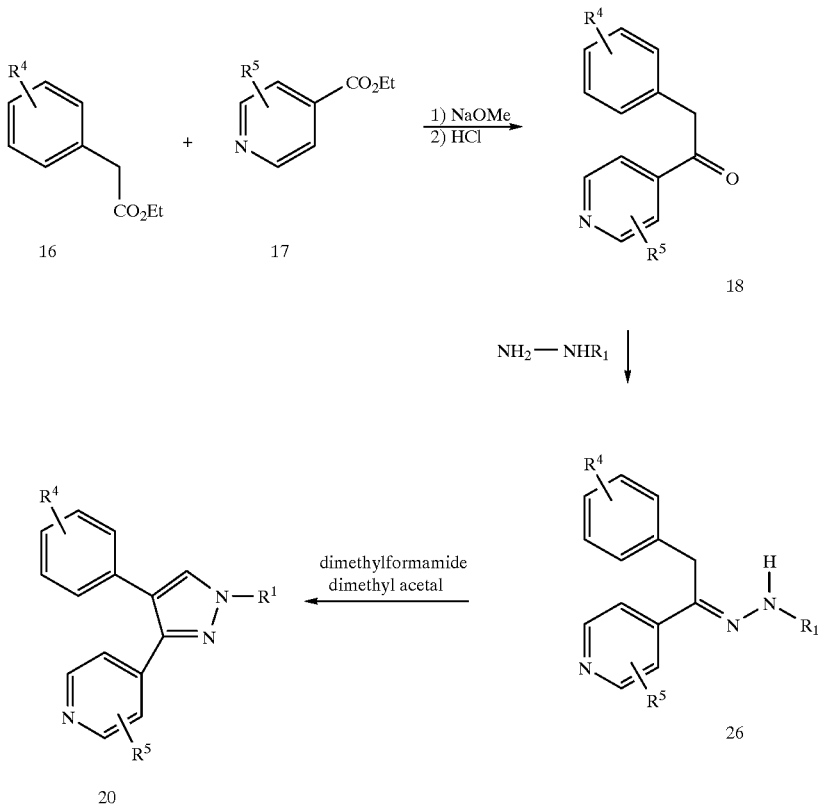

Scheme VI is similar to Scheme IV except that desoxybenzoin 18 is first reacted with hydrazine in a suitable solvent such as ethanol to yield hydrazine 26. Hydrazine 26 is then converted to pyrazole 20 (rather than a mixture of pyrazoles 20 and 21 as in Scheme IV) by treatment with an excess of dimethylformamide dimethyl acetal. In Scheme VI, $R^4$ and $R^1$ are as defined in Scheme V.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures. In some cases, the assigned structures were confirmed by nuclear Overhauser effect (NOE) experiments.

The following abbreviations are used:
HCl—hydrochloric acid
$MgSO_4$—magnesium sulfate
$Na_2SO_4$—sodium sulfate
$NaIO_4$—sodium periodate
$NaHSO_3$—sodium bisulfite
NaOH—sodium hydroxide
KOH—potassium hydroxide
$P_2O_5$—phosphorus pentoxide
MeOH—methanol
EtOH—ethanol
HOAc (or AcOH)—acetic acid
EtOAc—ethyl acetate
$H_2O$—water
$H_2O_2$—hydrogen peroxide
$CH_2Cl_2$—methylene chloride
NaOMe—sodium methoxide
h—hour
hr—hour
min—minutes
THF—tetrahydrofuran
TLC—thin layer chromatography
DSC—differential scanning calorimetry
b.p.—boiling point
m.p.—melting point
eq—equivalent

EXAMPLE 1

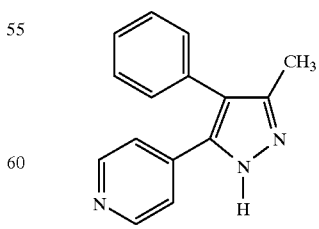

4-(3-methyl-4-phenyl-1H-pyrazol-5-yl)pyridine
Step 1: Preparation of 3-phenyl-4-(4-pyridyl)-3-butene-2-one 3-Phenyl-4-(4-pyridyl)-3-butene-2-one was prepared by the method of Reichert and Lechner, *Arzneim.-Forsch.* 15, 36 (1965), which is incorporated by reference herein.

Step 2: Preparation of 3-phenyl-4-(4-pyridyl)-3,4-epoxy-2-butanone

To a stirred solution of 3-phenyl-4-(4-pyridyl)-3-butene-2-one (step 1) (500 mg, 2.24 mmol) in methanol (10 ml) at room temperature was added an aqueous solution (9 ml) of sodium hydroxide (100 mg, 2.24 mmol) and hydrogen peroxide (0.5 ml of 30% aqueous solution, 4.4 mmol). After stirring for 2 hours, sodium chloride was added and the reaction was extracted with ethyl acetate. The combined organic layers were dried over magnesium sulfate, filtered, and concentrated in vacuo to provide the crude 3-phenyl-4-(4-pyridyl)-3,4-epoxy-2-butanone (385 mg, 65%) as an oil. This was used in the next step without further purification.

Step 3: Preparation of 4-(3-methyl-4-phenyl-1H-pyrazol-5-yl)pyridine

A solution of 3-phenyl-4-(4-pyridyl)-3,4-epoxy-2-butanone (step 2) (350 mg, 1.46 mmol) and anhydrous hydrazine (0.7 ml, 20 mmol) in ethanol (3 ml) was heated at reflux for 4 hours. The reaction was cooled, and the solvent was evaporated to dryness. The resulting residue was purified by chromatography (silica gel, 1:1 acetone/hexane) to give the desired product as a crystalline solid, which was recrystallized from ethyl acetate and hexane to give pure 4-(3-methyl-4-phenyl-1H-pyrazol-5-yl)pyridine (145 mg, 42%): m. p. 164–165° C.

Anal. Calc'd for $C_{15}H_{13}N_3$ (235.29) : C, 76.57; H, 5.57; N, 17.86. Found: C, 76.49; H, 5.45; N, 17.70.

The compounds of Examples 2 through 8 were synthesized in accordance with the chemistry described above (particularly in Scheme III) by selection of the corresponding starting reagents:

EXAMPLE 2

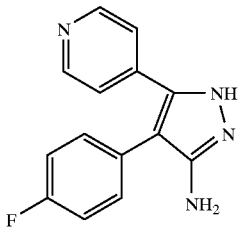

4-(4-fluorophenyl)-5-(4-pyridinyl)-1H-pyrazol-3-amine

The cyanoketone 1 of Scheme III wherein X is p-fluoro was synthesized according to the procedure of I. Lantos et al., *J. Org. Chem.*, 53, 4223–4227 (1988), which is incorporated herein by reference. A solution of the cyanoketone (10 g, 41 mmol), hydrazine hydrate (2.5 ml) and acetic acid (5.2 ml) in benzene (100 ml) was refluxed for 4 hours. The reaction was cooled and extracted with 3N HCl. The combined acid extracts were basified to pH 10 using concentrated ammonium hydroxide with cooling. The basic aqueous layer was extracted with methylene chloride and the combined organic extracts were dried over magnesium sulfate.

The drying agent was filtered and the filtrate concentrated in vacuo to give the crude 4-(4-fluorophenyl)-5-(4-pyridinyl)-1H-pyrazol-3-amine which was purified by recrystallization from ethyl acetate and hexane. Purified 4-(4-fluorophenyl)-5-(4-pyridinyl)-1H-pyrazol-3-amine had m.p. 178–180° C. (capillary).

Anal. Calc'd for $C_{14}H_{11}N_4F+0.25\ H_2O$: C, 64.99; H, 4.48; N, 21.65. Found: C, 64.99; H, 4.48; N, 21.54.

EXAMPLE 3

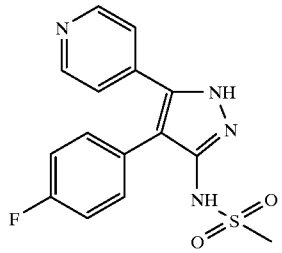

N-[4(4-fluorophenyl)-5-(4-pyridinyl)-1H-pyrazol-3-yl]methanesulfonamide

A solution of 4-(4-fluorophenyl)-5-(4-pyridinyl)-1H-pyrazol-3-amine prepared as set forth in Example 2 (200 mg, 0.77 mmol) and methanesulfonyl chloride (90 mg) in pyridine (5 ml) was stirred at room temperature overnight. The pyridine was removed in vacuo and the residue was treated with methylene chloride and water. The resultant precipitate was filtered to give N-[4(4-fluorophenyl)-5-(4-pyridinyl)-1H-pyrazol-3-yl]methanesulfonamide. Additional N-[4(4-fluorophenyl)-5-(4-pyridinyl)-1H-pyrazol-3-yl]methanesulfonamide was contained in the methylene chloride layer. The methylene chloride was stripped in vacuo and the residue purified by chromatography on silica gel using mixtures of ethyl acetate and methanol as eluents. The purified N-[4(4-fluorophenyl)-5-(4-pyridinyl)-1H-pyrazol-3-yl]methanesulfonamide had m.p. 168–170° C.

Anal. Calc'd for $CH_{15}H_{13}N_4SO_2F+0.25\ H_2O$: C, 53.48; H, 4.04; N, 16.63. Found: C, 53.41; H, 3.78; N, 16.52.

EXAMPLE 4

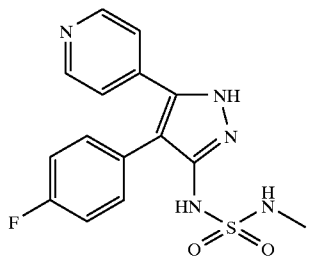

N-[4-(4-fluorophenyl)-5-(4-pyridinyl)-1H-pyrazol-3-yl]-N'-methylsulfamide

Methyl sulfamyl chloride was synthesized by refluxing a solution of methylsulfamic acid (1.0 g) in phosphorus oxychloride (10 mL) for 6 hours. The excess phosphorus oxychloride was removed in vacuo and the residual oil was used for the synthesis of the product without further treatment. A solution of 4-(4-fluorophenyl)-5-(4-pyridinyl)-1H-pyrazol-3-amine prepared as set forth in Example 2 (200 mg, 0.77 mmol) and approximately 1 mmol of the above oil in pyridine (5 ml) was stirred at room temperature for 2 hours. The reaction was stripped in vacuo and the residue purified by chromatography on silica gel using ethyl acetate and mixtures of ethyl acetate and methanol as eluents to give N-[4-(4-fluorophenyl)-5-(4-pyridinyl)-1H-pyrazol-3-1-yl]-N'-methylsulfamide as a crystalline solid, m. p. 194–195° C.

Anal. Calc'd for $C_{15}H_{14}N_5SO_2F+1.0\ H_2O$: C, 49.31; H, 4.41; N, 19.17. Found: C, 49.13; H, 3.97; N, 19.01.

EXAMPLE 5

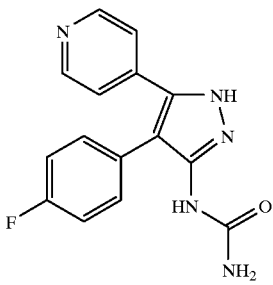

[4-(4-fluorophenyl)-5-(4-pyridinyl)-1H-pyrazol-3-yl] urea

A suspension of 4-(4-fluorophenyl)-5-(4-pyridinyl)-1H-pyrazol-3-amine prepared as set forth in Example 2 (200 mg, 0.77 mmol) in a solution of di-tert-butyl carbonate (185 mg, 0.9 mmol) and 4-dimethylaminopyridine (DMAP) (10 mg) in methylene chloride (10 ml) was stirred at room temperature for 20 minutes, during which time, the suspended material dissolved. N-Propylamine (50 mg) was added and stirring was continued at room temperature for 1 hour. The reaction was then refluxed for 15 minutes, cooled and stripped in vacuo. Treatment with ethyl acetate and hexane resulted in the deposition of crystals of the tert-butoxycarbonyl derivative, m.p. 183–184° C.

Anal. Calc'd for $C_{19}H_{19}N_4O_2F$: C, 64.40; H, 5.40; N, 15.81. Found: C, 64.66; H, 5.63; N, 15.63.

A solution of the tert-butoxycarbonyl derivative above (100 mg, 0.3 mmol) in tetrahydrofuran was treated with ammonia at 80° C. in a pressure bottle for 12 hours. The reaction was stripped in vacuo and the residue was purified by chromatography on silica gel eluting with mixtures of ethyl acetate and methanol. The purified [4-(4-fluorophenyl)-5-(4-pyridinyl)-1H-pyrazol-3-yl]urea thus obtained had m.p. 224–225° C.

Anal. Calc'd for $C_{15}H_{12}N_5O$: C, 60.60; H, 4.07; N, 23.56. Found: C, 60.21; H, 4.11; N, 23.30.

EXAMPLE 6

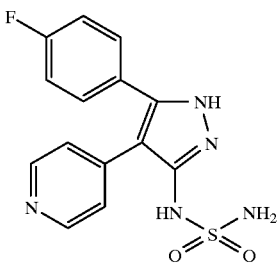

[4-(4-fluorophenyl)-5-(4-pyridinyl)-1H-pyrazol-3-yl] sulfamide

Sulfamyl chloride was synthesized from chlorosulfonyl isocyanate according to the procedure described by R. Graf in *Chemische Berichte*, p. 509 (1959), which is incorporated herein by reference. A solution of 4-(4-fluorophenyl)-5-(4-pyridinyl)-1H-pyrazol-3-amine prepared as set forth in Example 2 (200 mg, 0.77 mmol), sulfamyl chloride (100 mg, 0.8 mmol) and triethylamine (200 mg, 2 mmol) in benzene (5 ml) and acetonitrile (5 ml) was stirred at room temperature for 2 hours. The reaction was stripped in vacuo and residue was treated with water and basified to pH 7 with ammonium hydroxide. The resultant precipitate was purified by chromatography on silica gel using mixtures of ethyl acetate and methanol as eluents. The purified [4-(4-fluorophenyl)-5-(4-pyridinyl)-1H-pyrazol-3-yl]sulfamide thus obtained had m.p. 201–202° C.

Anal. Calc'd for $C_{14}H_{12}N_5SO_2F$: C, 50.44; H, 3.63; N, 21.01. Found: C, 50.43; H, 3.45; N, 20.89.

EXAMPLE 7

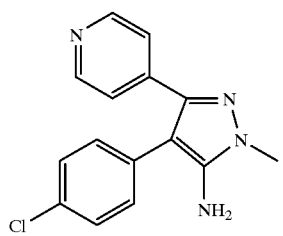

4-(4-chlorophenyl)-1-methyl-3-(4-pyridinyl)-1H-pyrazol-5-amine

A solution of cyanoketone 1 of Scheme III wherein X is p-chloro (1.5 g, 5.19 mmol), methylhydrazine (0.35 ml) and acetic acid (0.75 ml) in benzene (15 ml) was refluxed for 3.5 hours. The reaction was cooled and extracted with 3N HCl. The aqueous layer was concentrated on the rotary evaporator and then basified with ammonium hydroxide. The resultant precipitate was recrystallized from methanol to give pure 4-(4-chlorophenyl)-1-methyl-3-(4-pyridinyl)-1H-pyrazol-5-amine, m.p. 257–258° C.

Anal. Calc'd for $C_{15}H_{13}N_4Cl$: C, 63.27; H, 4.60; N, 19.68. Found: C, 62.93; H, 4.45; N, 19.64.

EXAMPLE 8

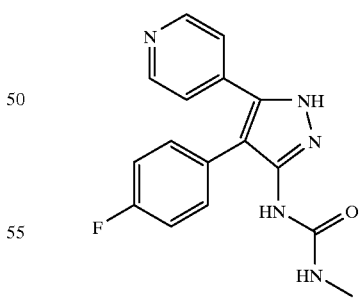

N-[4-(4-fluorophenyl)-5-(4-pyridinyl)-1H-pyrazol-3-yl]-N'-methylurea

A solution of 4-(4-fluorophenyl)-5-(4-pyridinyl)-1H-pyrazol-3-amine prepared as set forth in Example 2 (100 mg, 0.38 mmol), methyl isocyanate (22 mg, 0.39 mmol) and 4-dimethylaminopyridine (2.5 mg) in methylene chloride (10 ml) was stirred at room temperature for 30 minutes. The reaction was stripped in vacuo. The residue was triturated with hexane and the solid filtered to give pure N-[4-(4-fluorophenyl)-5-(4-pyridinyl)-1H-pyrazol-3-yl]-N'-methylurea, m. p. 212–213° C.

Anal. Calc'd for $C_{16}H_{14}N_5FO$: C, 61.73; H, 4.53; N, 22.50. Found: C, 61.63; H, 4.55; N, 22.47.

The compounds of Examples 9 through 11 were synthesized in accordance with the chemistry described above (particularly in Scheme IV) by selection of the corresponding starting reagents:

EXAMPLE 9

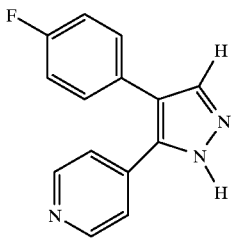

4-[4-(4-fluorophenyl)-1H-pyrazol-3-yl]pyridine

Step 1

Methyl isonicotinate (13.7 g, 0.1 mole) and ethyl 4-fluorophenylacetate (18.2 g, 1.0 mole) were mixed together, then sodium methoxide (8.1 g, 0.15 mole) was added. The mixture was heated to 60–70° C. for 24 hours while nitrogen was blown through the flask to eliminate methanol. Concentrated hydrochloric acid (50 mL) then was added and the reaction mixture was refluxed for 3 hours. After addition of water (30 mL), the reaction mixture was extracted with chloroform, and the water phase was neutralized to pH 6–7 with aqueous sodium hydroxide (1M). The precipitate formed was collected by filtration, washed with water and dried under vacuum to give 10 g of 2-(4-fluorophenyl)-1-(4'-pyridyl)-ethan-1-one (yield: 46%). $^1H$ NMR: consistent with the assigned structure and/or its tautomer.

Step 2

2-(4-fluorophenyl)-1(4'-pyridyl)-ethan-1-one prepared above (1 g) was dissolved in 50 mL tetrahydrofuran and N,N-dimethylformamide dimethyl acetal (5 mL) was added. The mixture was stirred at room temperature for 2 days. After evaporating the solvent, the solid obtained was washed with hexane and 1 g of the vinyl amine was obtained. This vinyl amine (0.5 g) was dissolved in ethanol (15 mL) and hydrazine hydrate (5 mL) was added. The mixture was stirred at 0° C. for 2 hours and then evaporated to dryness. After recrystallization from methanol/water, 400 mg of 4-[4-(4-fluorophenyl)-1H-pyrazol-3-yl]pyridine was obtained in 91% yield. MS, 240(M+1); $^1H$ NMR: consistent with the assigned structure;

Anal. Calc'd for $C_{14}H_{10}FN_3 \cdot 0.2H_2O$: C, 69.24; H, 4.32; N, 17.30. Found: C, 69.54; H, 4.06; N, 17.43.

EXAMPLE 10

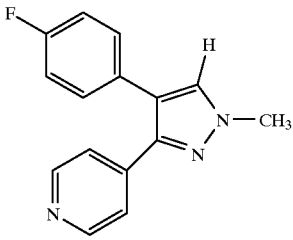

4-[4-(4-fluorophenyl)-1-methyl-1H-pyrazol-3-yl]pyridine

When methylhydrazine was substituted for hydrazine hydrate in Step 2 of Example 9, 4-[4-(4-fluorophenyl)-1-methyl-1H-pyrazol-3-yl]pyridine (the N-methyl derivative corresponding to the compound of Example 9) was obtained. Purification by recrystallization from toluene and hexane give the pure 4-[4-(4-fluorophenyl)-1-methyl-1H-pyrazol-3-yl]pyridine in 57% yield. MS m/z: 254 (M+1). $^1H$ NMR: consistent with the assigned structure. Anal. calc'd for $C_{15}H_{12}FN_3$: C, 71.13; H, 4.78; N, 16.69. Found: C, 70.99; H, 4.68; N, 16.65.

EXAMPLE 11

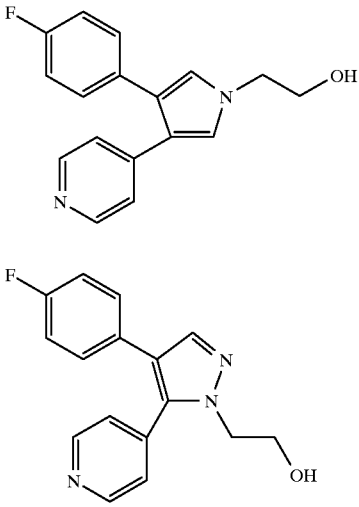

4-(4-fluorophenyl)-3-(4-pyridinyl)-1H-pyrazole-1-ethanol and 4-(4-fluorophenyl)-5-(4-pyridinyl)-1H-pyrazole-1-ethanol The procedure set forth in Example 9 was followed except that 2-hydroxyethyl hydrazine was substituted for hydrazine hydrate. 4-(4-Fluorophenyl)-3-(4-pyridinyl)-1H-pyrazole-1-ethanol and 4-(4-fluorophenyl)-5-(4-pyridinyl)-1H-pyrazole-1-ethanol were obtained as a mixture by recrystallization from toluene and hexane in 67% yield. $^1H$ NMR: consistent with the assigned structure. Mass spectrum, m/z: 284 (M+l). Anal. calc'd for $C_{16}H_{14}FN_3O$: C, 67.83; H, 4.98; N, 14.83. Found: C, 67.86; H, 5.04; N, 14.85.

The compounds of Examples 12 and 13 were synthesized in accordance with the chemistry described above (particularly in Scheme V) by selection of the corresponding starting reagents:

EXAMPLE 12

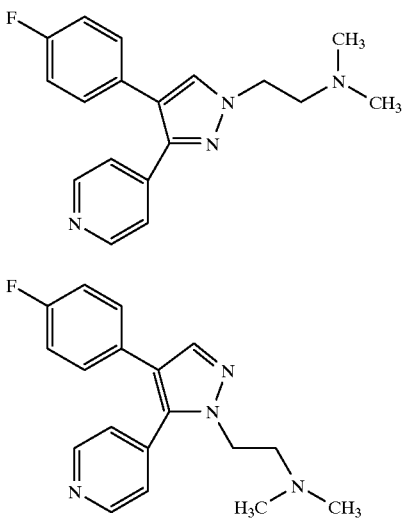

4-(4-fluorophenyl)-N,N-dimethyl-3-(4-pyridinyl)-1H-pyrazole-1-ethanamine and 4-(4-fluorophenyl)-N,N-dimethyl-5-(4-pyridinyl)-1H-pyrazole-1-ethanamine 4-(4-Fluorophenyl)-3-(4-pyridinyl)-1H-pyrazole-1-ethanol (or 4-(4-fluorophenyl)-5-(4-pyridinyl)-1H-pyrazole-1-ethanol) prepared as set forth in Example 11 (1.36 g) was dissolved in 30 mL pyridine and cooled to 0° C., whereupon methanesulfonyl chloride (0.6 mL) was added. After stirring at 0° C. for 12 hours, about 20 g of ice was added, and the mixture was extracted with toluene (300 ml). After evaporation, the residue was used directly without further purification. 0.7 g of the above obtained compound was dissolved in methanol (25 mL), and dimethylamine/THF solution (4M, 2 mL) was added. The reaction mixture was refluxed for 12 hours, then evaporated to dryness. The residue was purified by chromatography (methanol/dichloromethane 1:10). A mixture (0.59 g) of 4-(4-fluorophenyl)-N,N-dimethyl-3-(4-pyridinyl)-1H-pyrazole-1-ethanamine and 4-(4-fluorophenyl)-N,N-dimethyl-5-(4-pyridinyl)-1H-pyrazole-1-ethanamine were obtained. $^1$H NMR: consistent with the assigned structure. Mass spectrum, m/z: 311 (M+1). Anal. calc'd $C_{18}H_{19}N_4F \cdot 0.55H_2O$: C, 67.50; H, 6.33; N, 17.49. Found: C, 67.21; H, 6.46; N, 17.14.

EXAMPLE 13

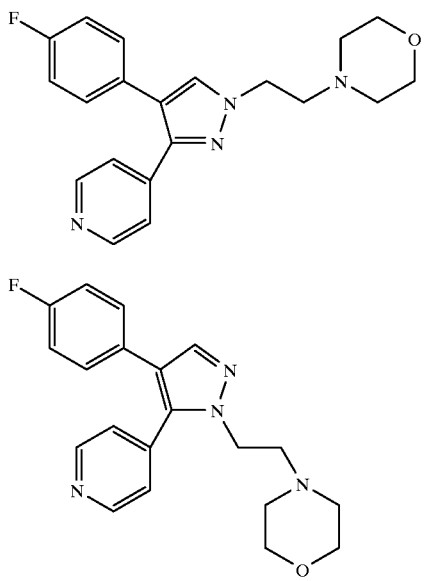

4-[2-[4-(4-fluorophenyl)-3-(4-pyridinyl)-1H-pyrazol-1-yl]ethyl]morpholine and

4-[2-[4-(4-fluorophenyl)-5-(4-pyridinyl)-1H-pyrazol-1-yl]ethyl]morpholine

The procedure set forth in Example 11 was followed, except that morpholine was substituted for dimethylamine, to produce a mixture of 4-[2-[4-(4-fluorophenyl)-3-(4-pyridinyl)-1H-pyrazol-1-yl]ethyl]morpholine and 4-[2-[4-(4-fluorophenyl)-5-(4-pyridinyl)-1H-pyrazol-1-yl]ethyl] morpholine. Mass spectrum, m/z: 353 (M+1).

Anal. calc'd for $C_{20}H_{21}N_4OF + 0.5H_2O$: C, 66.47; H, 6.14; N, 15.50. Found: C, 66.57; H, 6.27; N, 15.14.

The compound of Example 14 was synthesized in accordance with the chemistry described above (particularly in Scheme VI) by selection of the corresponding starting reagents:

EXAMPLE 14

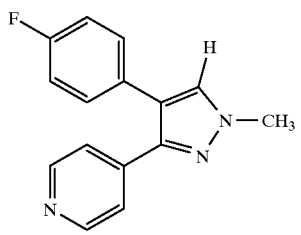

4-[4-(4-fluorophenyl)-1-methyl-1H-pyrazol-3-yl] pyridine 2-(4-fluorophenyl)-1-(4'-pyridyl)-ethan-1-one prepared as set forth in step 1 of Example 9 (0.5 g, 0.00232 moles) was mixed with of 98% methyl hydrazine (0.2 g, 0.00462 moles) in 10 mL of ethanol containing 0.1 mL of acetic acid in a 50 mL Erlenmeyer flask. After gentle boiling (30 minutes on a steam bath) a small sample was evacuated at high vacuum and examined by NMR to confirm completion of hydrazone formation. The reaction mixture was concentrated to a pasty mass and 3.6 mL of DMF dimethylacetal (0.027 moles) was then added and heated to 80° C. for 30 minutes, at which point a clear yellow viscous solution was obtained. The reaction was checked for completion (TLC or NMR) and concentrated and taken up in 20 mL of chloroform. After washing with water (10 mL), the organic layer was extracted with 15 mL of 10% HCl. The water layer was then treated with 0.5 g of activated charcoal at 70° C. for 10 minutes, filtered through celite, neutralized cautiously to pH 7–8 with vigorous stirring and cooling. The fine off-white precipitate was filtered and dried. NMR was found to be in agreement with the proposed structure. The precipitate, 4-[4-(4-fluorophenyl)-1-methyl-1H-pyrazol-3-yl]pyridine, obtained in quantitative yield was filtered, washed with ether and dried. Yield: 0.45 g (77%). Mass spectrum, m/z: 254. Anal. calc'd: C, 62.18; H, 4.52; N, 14.50. Found: C, 62.39; H, 4.07; N, 14.24.

EXAMPLE 15

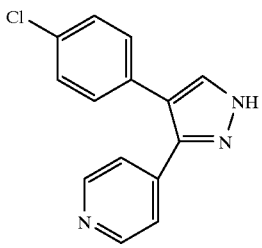

4-[4-(4-chlorophenyl)-1H-pyrazol-3-yl]pyridine

4-[4-(4-chlorophenyl)-1H-pyrazol-3-yl]pyridine was prepared according to the procedure set forth in Example 9 except that ethyl 4-chlorophenylacetate was substituted for ethyl 4-fluorophenylacetate; m.p. 204–207° C.

Anal. Calc'd: C, 65.76; H, 3.94; N, 16.43. Found: C, 65.44; H, 3.78; N, 16.04.

EXAMPLE 16

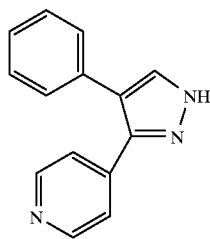

4-(4-phenyl-1H-pyrazol-5-yl)pyridine 4-(4-phenyl-1H-pyrazol-5-yl)pyridine can be prepared in accordance with the procedure set forth in Example 9 by substituting ethylphenylacetate for ethyl 4-fluorophenylacetate.

EXAMPLE 17

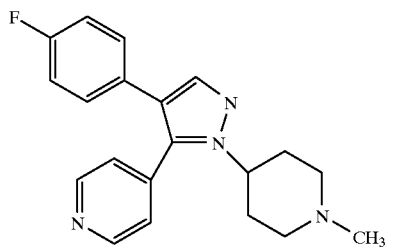

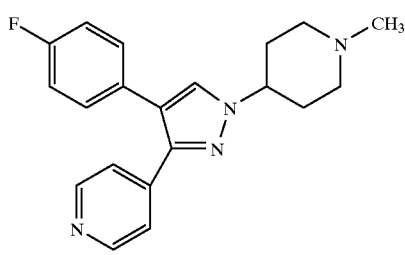

1-methyl-4-[2-[4-(4-fluorophenyl)-3-(4-pyridinyl)-1H-pyrazol-1-yl]]piperidine and 1-methyl-4-[2-[4-(4-fluorophenyl)-5-(4-pyridinyl)-1H-pyrazol-1-yl]piperidine This compound can be prepared using the procedure set forth for the synthesis of the compound of Example 11 by substituting 4-hydrazino-N-methylpiperidine for hydroxyethyl hydrazine. 4-Hydrazino-N-methylpiperidine is synthesized as disclosed in Ebnoether et al, Helv. Chim. Acta (1959) 42, 533, 541, 560. The resulting mixture is separated into the respective pure title compounds by chromatography on silica gel, eluting with methanol/dichloromethane (1:10), or other suitable solvent system.

BIOLOGICAL EVALUATION p38 Kinase Assay

Cloning of human p38a:

The coding region of the human p38a cDNA was obtained by PCR-amplification from RNA isolated from the human monocyte cell line THP.1. First strand cDNA was synthesized from total RNA as follows: 2 μg of RNA was annealed to 100 ng of random hexamer primers in a 10 μl reaction by heating to 70° C. for 10 minutes followed by 2 minutes on ice. cDNA was then synthesized by adding 1 μl of RNAsin (Promega, Madison Wis.), 2 μl of 50 mM dNTP's, 4 μl of 5× buffer, 2 μl of 100 mM DTT and 1 μl (200 U) of Superscript II™ AMV reverse transcriptase. Random primer, dNTP's and Superscript™ reagents were all purchased from Life-Technologies, Gaithersburg, Mass. The reaction was incubated at 42° C. for 1 hour. Amplification of p38 cDNA was performed by aliquoting 5 μl of the reverse transcriptase reaction into a 100 μl PCR reaction containing the following: 80 μl dH$_2$O, 2 μl 50 mM dNTP's, 1 μl each of forward and reverse primers (50 pmol/μl), 10 μl of 10× buffer and 1 μl Expand™ polymerase (Boehringer Mannheim). The PCR primers incorporated Bam HI sites onto the 5' and 3' end of the amplified fragment, and were purchased from Genosys. The sequences of the forward and reverse primers were 5'-GATCGAGGATTCATGTCTCAGGAGAGGCCCA-3' and 5'GATCGAGGATTCTCAGGACTCCATCTCTTC-3' respectively. The PCR amplification was carried out in a DNA Thermal Cycler (Perkin Elmer) by repeating 30 cycles of 94° C. for 1 minute, 60° C. for 1 minute and 68° C. for 2 minutes. After amplification, excess primers and unincorporated dNTP's were removed from the amplified fragment with a Wizard™ PCR prep (Promega) and digested with Bam HI (New England Biolabs). The Bam HI digested fragment was ligated into BamHI digested PGEX 2T plasmid DNA (PharmaciaBiotech) using T-4 DNA ligase (New England Biolabs) as described by T. Maniatis, *Molecular Cloning: A Laboratory Manual*, 2nd ed. (1989). The ligation reaction was transformed into chemically competent *E. coli* DH10B cells purchased from Life-Technologies following the manufacturer's instructions. Plasmid DNA was isolated from the resulting bacterial colonies using a Promega Wizard™ miniprep kit. Plasmids containing the appropriate Bam HI fragment were sequenced in a DNA Thermal Cycler (Perkin Elmer) with Prism™ (Applied Biosystems Inc.). cDNA clones were identified that coded for both human p38a isoforms (Lee et al. Nature 372, 739). One of the clones which contained the cDNA for p38a-2 (CSBP-2) inserted in the cloning site of pGEX 2T, 3' of the GST coding region was designated pMON 35802. The sequence obtained for this clone is an exact match of the cDNA clone reported by Lee et al. This expression plasmid allows for the production of a GST-p38a fusion protein.

Expression of human p38a:

GST/p38a fusion protein was expressed from the plasmid pMON 35802 in *E. coli*, stain DH10B (Life Technologies, Gibco-BRL). Overnight cultures were grown in Luria Broth (LB) containing 100 mg/ml ampicillin. The next day, 500 ml of fresh LB was inoculated with 10 ml of overnight culture, and grown in a 2 liter flask at 37° C. with constant shaking until the culture reached an absorbance of 0.8 at 600 nm. Expression of the fusion protein was induced by addition of isopropyl b-D-thiogalactosidse (IPTG) to a final concentration of 0.05 mM. The cultures were shaken for three hours at room temperature, and the cells were harvested by centrifugation. The cell pellets were stored frozen until protein purification.

Purification of p38 Kinase-α:

All chemicals were from Sigma Chemical Co. unless noted. Twenty grams of *E. coli* cell pellet collected from five 1 L shake flask fermentations was resuspended in a volume of PBS (140 mM NaCl, 2.7 mM KCl, 10 mM $Na_2HPO_4$, 1.8 mM $KH_2PO_4$, pH 7.3) up to 200 ml. The cell suspension was adjusted to 5 mM DTT with 2 M DTT and then split equally into five 50 ml Falcon conical tubes. The cells were sonnicated (Ultrasonics model W375) with a 1 cm probe for 3×1 minutes (pulsed) on ice. Lysed cell material was removed by centrifugation (12,000×g, 15 minutes) and the clarified supernatant applied to glutathione-sepharose resin (Pharmacia).

Glutathione-Sepharose Affinity Chromatography:

Twelve ml of a 50% glutathione sepharose-PBS suspension was added to 200 ml clarified supernatant and incubated batchwise for 30 minutes at room temperature. The resin was collected by centrifugation (600×g, 5 min) and washed with 2×150 ml PBS/1% Triton X-100, followed by 4×40 ml PBS. To cleave the p38 kinase from the GST-p38 fusion protein, the glutathione-sepharose resin was resuspended in 6 ml PBS containing 250 units thrombin protease (Pharmacia, specific activity>7500 units/mg) and mixed gently for 4 hours at room temperature. The glutathione-sepharose resin was removed by centrifugation (600×g, 5 min) and washed 2×6 ml with PBS. The PBS wash fractions and digest supernatant containing p38 kinase protein were pooled and adjusted to 0.3 mM PMSF.

Mono Q Anion Exchange Chromatograhy:

The thrombin-cleaved p38 kinase was further purified by FPLC-anion exchange chromatography. Thrombin-cleaved sample was diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column was eluted with a 160 ml 0.1 M–0.6 M NaCl/Buffer A gradient (2 ml/minute flowrate). The p38 kinase peak eluting at 200 mM NaCl was collected and concentrated to 3–4 ml with a Filtron 10 concentrator (Filtron Corp.).

Sephacryl S100 Gel Filtration Chromatography:

The concentrated Mono Q- p38 kinase purified sample was purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein was eluted from the column with Buffer B at a 0.5 ml/minute flowrate and protein was detected by absorbance at 280 nm. Fractions containing p38 kinase (detected by SDS-polyacrylamide gel electrophoresis) were pooled and frozen at −80° C. Typical purified protein yields from 5 L *E. coli* shake flasks fermentations were 35 mg p38 kinase.

In Vitro Assay

The ability of compounds to inhibit human p38 kinase alpha was evaluated using two in vitro assay methods. In the first method, activated human p38 kinase alpha phosphorylates a biotinylated substrate, PHAS-I (phosphorylated heat and acid stable protein-insulin inducible), in the presence of gamma $^{32}$P-ATP ($^{32}$P-ATP). PHAS-I was biotinylated prior to the assay and provides a means of capturing the substrate which is phosphorylated during the assay. p38 Kinase was activated by MKK6. Compounds were tested in 10 fold serial dilutions over the range of 100 μM to 0.001 μM using 1% DMSO. Each concentration of inhibitor was tested in triplicate.

All reactions were carried out in 96 well polypropylene plates. Each reaction well contained 25 mM HEPES pH 7.5, 10 mM magnesium acetate and 50 μM unlabeled ATP. Activation of p38 was required to achieve sufficient signal in the assay. Biotinylated PHAS-I was used at 1–2 μg per 50 μl reaction volume, with a final concentration of 1.5 μM. Activated human p38 kinase alpha was used at 1 μg per 50 μl reaction volume representing a final concentration of 0.3 μM. Gamma $^{32}$P-ATP was used to follow the phosphorylation of PHAS-I. $^{32}$P-ATP has a specific activity of 3000 Ci/mmol and was used at 1.2 μCi per 50 μl reaction volume. The reaction proceeded either for one hour or overnight at 30° C.

Following incubation, 20 μl of reaction mixture was transferred to a high capacity streptavidin coated filter plate (SAM-streptavidin-matrix, Promega) prewetted with phosphate buffered saline. The transferred reaction mix was allowed to contact the streptavidin membrane of the Promega plate for 1–2 minutes. Following capture of biotinylated PHAS-I with $^{32}$P incorporated, each well was washed to remove unincorporated $^{32}$P-ATP three times with 2M NaCl, three washes of 2M NaCl with 1% phosphoric, three washes of distilled water and finally a single wash of 95% ethanol. Filter plates were air dried and 20 μl of scintillant was added. The plates were sealed and counted.

A second assay format was also employed that is based on p38 kinase alpha induced phosphorylation of EGFRP (epidermal growth factor receptor peptide, a 21 mer) in the presence of $^{33}$P-ATP. Compounds were tested in 10 fold serial dilutions over the range of 100 μM to 0.001 μM in 1% DMSO. Each concentration of inhibitor was tested in triplicate. Compounds were evaluated in 50μl reaction volumes in the presence of 25 mM Hepes pH 7.5, 10 mM magnesium acetate, 4% glycerol, 0.4% bovine serum albumin, 0.4 mM DTT, 50 μM unlabeled ATP, 25 μg EGFRP (200 μM), and 0.05 uCi gamma $^{33}$P-ATP. Reactions were initiated by addition of 0.09 μg of activated, purified human GST-p38 kinase alpha. Activation was carried out using GST-MKK6 (5:1,p38:MKK6) for one hour at 30° C. in the presence of 50 μM ATP. Following incubation for 60 minutes at room temperature, the reaction was stopped by addition of 150 μl of AG 1×8 resin in 900 mM sodium formate buffer, pH 3.0 (1 volume resin to 2 volumes buffer). The mixture was mixed three times with pipetting and the resin was allowed to settle. A total of 50 μl of clarified solution head volume was transferred from the reaction wells to Microlite-2 plates. 150 μl of Microscint 40 was then added to each well of the Microlite plate, and the plate was sealed, mixed, and counted.

TNF Cell Assays

Method of Isolation of Human Peripheral Blood Mononuclear Cells:

Human whole blood was collected in Vacutainer tubes containing EDTA as an anticoagulant. A blood sample (7 ml) was carefully layered over 5 ml PMN Cell Isolation Medium (Robbins Scientific) in a 15 ml round bottom centrifuge tube. The sample was centrifuged at 450–500×g for 30–35 minutes in a swing out rotor at room temperature. After centrifugation, the top band of cells were removed and washed 3 times with PBS w/o calcium or magnesium. The cells were centrifuged at 400×g for 10 minutes at room temperature. The cells were resuspended in Macrophage Serum Free Medium (Gibco BRL) at a concentration of 2 million cells/ml.

LPS Stimulation of Human PBMs:

PBM cells (0.1 ml, 2 million/ml) were co-incubated with 0.1 ml compound (10–0.41 μM, final concentration) for 1 hour in flat bottom 96 well microtiter plates. Compounds were dissolved in DMSO initially and diluted in TCM for a final concentration of 0.1% DMSO. LPS (Calbiochem, 20 ng/ml, final concentration) was then added at a volume of 0.010 ml. Cultures were incubated overnight at 37° C. Supernatants were then removed and tested by ELISA for TNF-α and IL1-b. Viability was analyzed using MTS. After 0.1 ml supernatant was collected, 0.020 ml MTS was added to remaining 0.1 ml cells. The cells were incubated at 37° C. for 2–4 hours, then the O.D. was measured at 490–650 nM.

Maintenance and Differentiation of the U937 Human Histiocytic Lymphoma Cell Line:

U937 cells (ATCC) were propagated in RPMI 1640 containing 10% fetal bovine serum, 100 IU/ml penicillin, 100 μg/ml streptomycin, and 2 mM glutamine (Gibco). Fifty million cells in 100 ml media were induced to terminal monocytic differentiation by 24 hour incubation with 20 ng/ml phorbol 12-myristate 13-acetate (Sigma). The cells were washed by centrifugation (200×g for 5 min) and resuspended in 100 ml fresh medium. After 24–48 hours, the cells were harvested, centrifuged, and resuspended in culture medium at 2 million cells/ml.

LPS Stimulation of TNF production by U937 Cells:

U937 cells (0.1 ml, 2 million/ml) were incubated with 0.1 ml compound (0.004–50 μM, final concentration) for 1 hour in 96 well microtiter plates. Compounds were prepared as 10 mM stock solutions in DMSO and diluted in culture medium to yield a final DMSO concentration of 0.1% in the cell assay. LPS (E coli, 100 ng/ml final concentration) was then added at a volume of 0.02 ml. After 4 hour incubation at 37° C., the amount of TNF-α released in the culture medium was quantitated by ELISA. Inhibitory potency is expressed as IC50 (μM).

Rat Assay

The efficacy of the novel compounds in blocking the production of TNF also was evaluated using a model based on rats challenged with LPS. Male Harlen Lewis rats [Sprague Dawley Co.] were used in this model. Each rat weighed approximately 300 g and was fasted overnight prior to testing. Compound administration was typically by oral gavage (although intraperitoneal, subcutaneous and intravenous administration were also used in a few instances) 1 to 24 hours prior to the LPS challenge. Rats were administered 30 μg/kg LPS [salmonella typhosa, Sigma Co.] intravenously via the tail vein. Blood was collected via heart puncture 1 hour after the LPS challenge. Serum samples were stored at −20° C. until quantitative analysis of TNF-α by Enzyme Linked-Immuno-Sorbent Assay ("ELISA") [Biosource]. Additional details of the assay are set forth in Perretti, M., et al., Br. J. Pharmacol. (1993), 110, 868–874, which is incorporated by reference in this application.

Mouse Assay

Mouse Model Of LPS-Induced TNF Alpha Production:

TNF alpha was induced in 10–12 week old BALB/c female mice by tail vein injection with 100 ng lipopolysaccharide (from S. Typhosa) in 0.2 ml saline. One hour later mice were bled from the retroorbital sinus and TNF concentrations in serum from clotted blood were quantified by ELISA. Typically, peak levels of serum TNF ranged from 2–6 ng/ml one hour after LPS injection.

The compounds tested were administered to fasted mice by oral gavage as a suspension in 0.2 ml of 0.5% methylcellulose and 0.025% Tween 20 in water at 1 hour or 6 hours prior to LPS injection. The 1 hour protocol allowed evaluation of compound potency at Cmax plasma levels whereas the 6 hour protocol allowed estimation of compound duration of action. Efficacy was determined at each time point as percent inhibition of serum TNF levels relative to LPS injected mice that received vehicle only.

Induction And Assessment of Collagen-Induced Arthritis In Mice:

Arthritis was induced in mice according to the procedure set forth in J. M. Stuart, Collagen Autoimmune Arthritis, Annual Rev. Immunol. 2:199 (1984), which is incorporated herein by reference. Specifically, arthritis was induced in 8–12 week old DBA/1 male mice by injection of 50 μg of chick type II collagen (CII) (provided by Dr. Marie Griffiths, Univ. of Utah, Salt Lake City, Utah) in complete Freund's adjuvant (Sigma) on day 0 at the base of the tail. Injection volume was 100 μl. Animals were boosted on day 21 with 50 μg of CII in incomplete Freund's adjuvant (100 μl volume). Animals were evaluated several times each week for signs of arthritis. Any animal with paw redness or swelling was counted as arthritic. Scoring of arthritic paws was conducted in accordance with the procedure set forth in Wooley et al., Genetic Control of Type II Collagen Induced Arthritis in Mice: Factors Influencing Disease Suspectibility and Evidence for Multiple MHC Associated Gene Control., Trans. Proc., 15:180 (1983). Scoring of severity was carried out using a score of 1–3 for each paw (maximal score of 12/mouse). Animals displaying any redness or swelling of digits or the paw were scored as 1. Gross swelling of the whole paw or deformity was scored as 2. Ankylosis of joints was scored as 3. Animals were evaluated for 8 weeks. 8–10 animals per group were used.

Preparation And Administration of Compounds:

The compounds tested on mice having collagen-induced arthritis were prepared as a suspension in 0.5% methylcelluose (Sigma, St. Louis, Mo.), 0.025% Tween 20 (Sigma). The compound suspensions were administered by oral gavage in a volume of 0.1 ml b.i.d. Administration began on day 20 post collagen injection and continued daily until final evaluation on day 56. Scoring of arthritic paws was conducted as set forth above.

Results obtained using the above-described assays are set forth in Table I below. p38 assay and U937 cell assay results are expressed as $IC_{50}$ ($\mu$m). Mouse-LPS assay results are expressed as percent inhibition.

TABLE I

| Example | P38α[1] ($\mu$M) | p38α[2] ($\mu$M) | U937 ($\mu$M) | mLPS (6 h @ 30 mpk) |
|---|---|---|---|---|
| 1 | 30.00 | 13.35 | 10.00 | |
| 2 | | 6.21 | 10.61 | |
| 3 | | 2.55 | >10.00 | |
| 4 | | 0.23 | 4.70 | 54 |
| 5 | 1.98 | | 5.53 | |
| 6 | | | 10.00 | |
| 7 | | 5.48 | 10.00 | |
| 8 | | | 10.00 | |
| 9 | 2.44 | 3.46 | 0.6474 | 42 |
| 10 | 7.23 | 0.4 | 1.5987 | 76 |
| 11 | 0.695 | 10 | 40 | |
| 12 | 0.941 | 10 | −5 | |
| 13 | 0.86 | >10 | 22 | |
| 15 | 5.9 | 0.75 | | 32 |

[1]p38α in vitro results based on PHAS-I assay procedure
[2]p38α in vitro results based on EGFRP assay procedure Also embraced within this invention is a class of pharmaceutical compositions comprising the active compounds of this invention in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically.

For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules. The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection. The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The pharmaceutical compositions may contain active ingredients in the range of about 0.1 to 1000 mg, preferably in the range of about 7.0 to 350 mg. A daily dose of about 0.01 to 100 mg/kg body weight, preferably between about 0.1 and about 50 mg/kg body weight and most preferably between about 0.5 to 30 mg/kg body weight, may be appropriate. The daily dose can be administered in one to four doses per day. In the case of skin conditions, it may be preferable to apply a topical preparation of compounds of this invention to the affected area two to four times a day. For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All patent documents listed herein are incorporated by reference. Although this invention has been described with respect to specific embodiments, the details of these embodiments are not to be construed as limitations.

What is claimed is:

1. A compound of Formula I

(I)

wherein

R$^1$ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and R$^2$ is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and Ar$^1$ is aryl unsubstituted or substituted with one or more radicals independently selected from halo, alkyl, alkenyl alkynyl, alkoxy, alkenoxy, alkyldioxy, alkylthio, alkylsulfinyul, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr$^2$ is pyridinyl, pyrimidinyl or quinolinyl unsubstituted or substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, alkynylamino, and aralkylamino; or or a pharmaceutically-acceptable salt or a tautomer thereof;

with the proviso that when HetAr$^2$ is pyridinyl, R$^2$ is selected from hydrido, alkyl, alkenyl, alkynyl, heterocyclyl, haloalkyl, heterocyclylalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy.

2. A compound of claim 1 wherein

R$^1$ is selected from hydrido, lower alkyl, lower cycloalkyl, lower cycloalkylalkylene, lower haloalkyl, lower hydroxyalkyl, lower alkenyl, lower alkynyl, lower heterocyclyl, lower aralkyl, lower alkoxyalkyl, lower mercaptoalkyl, lower alkylthioalkylene, amino, lower alkylamino, lower arylamino, lower aminoalkyl, lower alkylaminoalkylene, lower heterocyclylalkylene, lower aminocarbonylalkylene, and lower alkylaminocarbonylalkylene; and R$^2$ is selected from hydrido, lower alkyl, lower alkenyl, lower alkynyl, lower haloalkyl, lower heterocyclyl, lower heterocyclylalkylene, amino, lower alkylamino, lower alkynylamino, lower aminoalkyl, lower alkylthio, lower carboxy, lower alkoxycarbonyl, lower carboxyalkyl, lower aminocarbonylamino, lower alkylaminocarbonylamino, lower alkylsulfonyl, lower aminosulfonyl, lower alkylsulfonylamino, lower aminosulfonylamino, and lower alkylaminosulfonylamino, wherein the heterocyclyl and heterocyclylalkyl groups are unsubstituted or substituted with one or more radicals independently selected from lower alkylthio, lower alkylsulfonyl, lower alkylsulfinyl, halo, lower alkyl, lower alkoxy, aryloxy, lower heterocyclyl, lower haloalkyl, amino, and cyano; and Ar$^1$ is selected from phenyl, biphenyl, and naphthyl, wherein Ar$^1$ is unsubstituted or substituted with one or more radicals independently selected from lower alkylthio, lower alkylsulfonyl, aminosulfonyl, halo, lower alkyl, lower alkenyl, lower alkynyl, lower alkylsulfinyl, cyano, lower alkoxycarbonyl, aminocarbonyl, formyl, lower alkylcarbonylamino, lower haloalkyl, lower alkoxy, lower alkenyloxy, lower alkyldioxy, amino, lower alkylamino, lower aminoalkyl, arylamino, nitro, and halosulfonyl; and HetAr$^2$ is pyridinyl or pyrimidinyl unsubstituted or substituted with one or more radicals independently selected from lower alkylthio, lower alkylsulfonyl, lower alkylsulfinyl, halo, lower alkyl, lower heterocyclyl, lower alkoxy, lower aralkoxy, lower haloalkyl, amino, cyano, lower aralkyl, lower alkylamino, lower cycloalkylamino, lower arylamino, lower alkynylamino, and lower aralkylamino; or a pharmaceutically-acceptable salt or tautomer thereof.

3. A Compound of claim 2 wherein $R^1$ is selected from hydrido, methyl, ethyl, isopropyl, tert-butyl, isobutyl, trichloroethyl, pentafluoroethyl, heptafluoropropyl, difluoroethyl, difluoropropyl, dichloroethyl, dichloropropyl, vinyl, allyl, ethynyl, propargyl, morpholinyl, piperidinyl, piperazinyl, benzyl, phenylethyl, morpholinomethyl, morpholinoethyl, pyrrolidinylmethyl, piperazinylmethyl, piperidinylmethyl, pyridinylmethyl, thienylmethyl, methoxymethyl, ethoxymethyl, amino, methylamino, dimethylamino, phenylamino, methylaminomethyl, dimethylaminoethyl, methylaminoethyl, dimethylaminoethyl, cyclopropyl, cyclopentyl, cyclohexyl, cyclohexylmethyl, hydroxymethyl, hydroxyethyl, methylthio, and methylthiomethyl; and $R^2$ is selected from hydrido, methyl, ethyl, propyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, amino, N-methylamino, N,N-dimethylamino, ethynylamino, propargylamino, piperidinyl, piperazinyl, morpholinomethyl, pyrrolidinylmethyl, piperazinylmethyl, piperidinylmethyl, pyridinylmethyl, thienylmethyl, thiazolylmethyl, oxazolylmethyl, pyrimidinylmethyl, quinolylmethyl, isoquinolinylmethyl, imidazolylmethyl, benzimidazolylmethyl, furylmethyl, pyrazinylmethyl, aminocarbonylamino, methylaminocarbonylamino, dimethylaminocarbonylamino, ethylaminocarbonylamino, diethylaminocarbonylamino, methylsulfonylamino, ethylsulfonylamino, aminosulfonylamino, methylaminosulfonylamino, dimethylaminosulfonylamino, ethylaminosulfonylamino, and diethylaminosulfonylamino; and Ar$^1$ is selected from phenyl, biphenyl, and naphthyl, wherein Ar$^1$ is unsubstituted or substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, allyl, vinyl, ethynyl, propargyl, methoxy, ethoxy, propyloxy, n-butoxy, amino, methylamino, ethylamino, dimethylamino, diethylamino, aminomethyl, aminoethyl, N-methyl, N-phenylamino, phenylamino, diphenylamino, nitro, and chlorosulfonyl; and HetAr$^2$ is selected from pyridinyl and pyrimidinyl, wherein HetAr$^2$ is unsubstituted or substituted with one or more radicals independently selected from methylthio, methylsulfinyl, methylsulfonyl, fluoro, chloro, bromo, methyl, ethyl, isopropyl, tert-butyl, isobutyl, methoxyl, ethoxyl, phenoxyl, benzoxyl, phenethyl, trifluoromethyl, fluoromethyl, difluoromethyl, amino, benzylamino, propargylamino, cyclopropylamino, cyclobutylamino, cyclopentylamino, and cyano; or a pharmaceutically-acceptable salt or tautomer thereof.

4. A compound of claim 3 wherein $R^1$ is hydrido, methyl, ethyl, hydroxyethyl, propargyl, dimethylaminoethyl or morpholinoethyl; and $R^2$ is selected from hydrido, methyl, ethyl, amino, aminocarbonylamino, methylaminocarbonylamino, methylsulfonylamino, aminosulfonylamino, and methylaminosulfonylamino; and Ar$^1$ is phenyl unsubstituted or substituted with one or more radicals independently selected from methylthio, methylsulfinyl, methylsulfonyl, fluoro, chloro, bromo, aminosulfonyl, methyl, ethyl, isopropyl, tert-butyl, isobutyl, cyano, methoxycarbonyl, ethoxycarbonyl, aminocarbonyl, methylcarbonylamino, trifluoromethyl, difluoromethyl, fluoromethyl, trichloromethyl, dichloromethyl, chloromethyl, methoxy, ethoxy, propyloxy, n-butoxy, amino, methylamino, ethylamino, dimethylamino, diethylamino, aminomethyl, aminoethyl, N-methyl, N-phenylamino, phenylamino, diphenylamino, nitro, and chlorosulfonyl; and HetAr$^2$ is unsubstituted or substituted with one or more radicals independently selected from methylthio, methylsulfinyl, methylsulfonyl, fluoro, chloro, bromo, methyl, ethyl, isopropyl, tert-butyl, isobutyl, methoxyl, ethoxyl, phenoxyl, benzoxyl, trifluoromethyl, fluoromethyl, difluoromethyl, amino, propargylamino, and cyano; or a pharmaceutically-acceptable salt or a tautomer thereof.

5. A compound of claim 4 wherein $R^1$ is hydrido or methyl; and $R^2$ is hydrido or methyl; and Ar$^1$ is phenyl which is unsubstituted or substituted with one or more radicals independently selected fluoro, chloro, methyl, ethyl, trifluoromethyl, methoxy, ethoxy, dimethylamino, and nitro; and HetAr$^2$ is unsubstituted or substituted with one or more radicals independently selected from methyl, chloro, fluoro, and trifluoromethyl; or a pharmaceutically-acceptable salt or tautomer thereof.

6. A compound of claim 1 wherein $R^2$ is hydrido.

7. A compound of claim 2 wherein $R^2$ is hydrido.

8. A compound of claim 3 wherein $R^2$ is hydrido.

9. A compound of claim 4 wherein $R^2$ is hydrido.

10. A compound of claim 5 wherein $R^2$ is hydrido.

11. A compound of claim 1 wherein HetAr$^2$ is unsubstituted or substituted with pyridinyl.

12. A compound of claim 2 wherein HetAr$^2$ is unsubstituted or substituted with pyridinyl.

13. A compound of claim 3 wherein HetAr$^2$ is unsubstituted or substituted with pyridinyl.

14. A compound of claim 4 wherein HetAr² is unsubstituted or substituted with pyridinyl.

15. A compound of claim 5 wherein HetAr² is unsubstituted or substituted with pyridinyl.

16. A compound of claim 1 wherein R² is hydrido, Ar¹ is unsubstituted or substituted with phenyl, and HetAr² is unsubstituted or substituted with pyridinyl.

17. A compound of claim 2 wherein R² is hydrido, Ar¹ is unsubstituted or substituted phenyl, and HetAr² is unsubstituted or substituted with pyridinyl.

18. A compound of claim 3 wherein R² is hydrido, Ar¹ is unsubstituted or substituted with phenyl, and HetAr² is unsubstituted or substituted with pyridinyl.

19. A compound of claim 4 wherein R² is hydrido and HetAr² is unsubstituted or substituted with pyridinyl.

20. A compound of claim 5 wherein R² is hydrido and HetAr² is unsubstituted or substituted with pyridinyl.

21. A compound of claim 4 selected from the compounds, their tautomers and their pharmaceutically acceptable salts, of the group consisting of
4-(3-methyl-4-phenyl-1H-pyrazol-5-yl)pyridine;
4-(4-fluorophenyl)-5-(4-pyridinyl)-1H-pyrazol-3-amine;
N-[4(4-fluorophenyl)-5-(4-pyridinyl)-1H-pyrazol-3-yl]methanesulfonamide;
N-[4-(4-fluorophenyl)-5-(4-pyridinyl)-1H-pyrazol-3-yl]-N'-methylsulfamide;
[4-(4-fluorophenyl)-5-(4-pyridinyl)-1H-pyrazol-3-yl]urea;
[4-(4-fluorophenyl)-5-(4-pyridinyl)-1H-pyrazol-3-yl]sulfamide;
4-(4-chlorophenyl)-1-methyl-3-(4-pyridinyl)-1H-pyrazol-5-amine;
N-[4-(4-fluorophenyl)-5-(4-pyridinyl)-1H-pyrazol-3-yl]-N'-methylurea;
4-[4-(4-fluorophenyl)-1H-pyrazol-3-yl]pyridine;
4-[4-(4-fluorophenyl)-1-methyl-1H-pyrazol-3-yl]pyridine;
4-(4-fluorophenyl)-3-(4-pyridinyl)-1H-pyrazole-1-ethanol;
4-(4-fluorophenyl)-N,N-dimethyl-3-(4-pyridinyl)-1H-pyrazole-1-ethanamine;
4-[2-[4-(4-fluorophenyl)-3-(4-pyridinyl)-1H-pyrazol-1-yl]ethyl]morpholine;
4-[4-(4-chlorophenyl)-1H-pyrazol-3-yl]pyridine;
1-methyl-4-[2-[4-(4-fluorophenyl)-3-(4-pyridinyl)-1H-pyrazol-1-yl]]piperidine; and
1-methyl-4-[2-[4-(4-fluorophenyl)-5-(4-pyridinyl)-1H-pyrazol-1-yl]piperidine.

22. A compound of Formula I

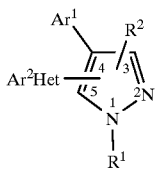

(I)

wherein
R¹ is selected from hydrido, lower alkyl, lower cycloalkyl, lower cycloalkylalkylene, lower haloalkyl, lower hydroxyalkyl, lower alkynyl, lower aralkyl, lower alkoxyalkyl, lower mercaptoalkyl, lower alkylthioalkylene, amino, lower alkylamino, lower arylamino, lower aminoalkyl, lower alkylaminoalkylene, lower heterocyclylalkylene, lower aminocarbonylalkylene, and lower alkylaminocarbonylalkylene; and
R² is selected from hydrido, lower alkyl, lower cycloalkyl, lower cycloalkenyl, aryl selected from phenyl and biphenyl, lower aralkyl, lower haloalkyl, lower heterocyclyl, lower heterocyclylalkylene, lower aminocarbonylamino, lower alkylaminocarbonylamino, sulfonyl, lower alkylsulfonylamino, lower aminosulfonylamino, and lower alkylaminosulfonylamino, wherein the cycloalkyl, aryl and heterocyclyl groups are unsubstituted or substituted with one or more radicals independently selected from lower alkylthio, lower alkylsulfonyl, lower alkylsulfinyl, halo, lower alkyl, lower alkoxy, aryloxy, lower heterocyclyl, lower haloalkyl, amino, and cyano; and Ar¹ is phenyl unsubstituted or substituted with one or more radicals independently selected from halo, lower alkyl, lower alkenyl, lower alkynyl, lower alkoxy, lower alkylthio, lower alkylsulfinyl, lower alkylsulfonyl, amino, aminocarbonyl, cyano, lower alkoxycarbonyl, formyl, aminosufonyl, lower alkylamino, nitro, lower arylamino, lower alkylcarbonylamino, halosulfonyl, lower aminoalkyl, and lower haloalkyl; and HetAr² is pyridinyl unsubstituted or substituted with one or more radicals independently selected from lower alkylthio, lower alkylsulfonyl, lower alkylsulfinyl, halo, lower alkyl, lower heterocyclyl, lower alkoxy, lower aralkoxy, lower haloalkyl, amino, cyano, lower aralkyl, lower alkylamino, lower cycloalkylamino, lower aralkylamino, lower arylamino; or a pharmaceutically-acceptable salt or a tautomer thereof.

23. A compound of claim 22 wherein
R¹ is hydrido, methyl, hydroxyethyl, dimethylaminoethyl, propargyl, or morpholinoethyl; and
R² is selected from hydrido, methyl, ethyl, amino, aminocarbonylamino, methylaminocarbonylamino, methylsulfonylamino, aminosulfonylamino, and methylaminosulfonylamino.

24. A compound of claim 22 wherein R² is hydrido.

25. A compound of claim 22 wherein Ar¹ is phenyl substituted with one or more halogen radicals.

26. A compound of claim 22 wherein R² is hydrido and Ar¹ is phenyl substituted with one or more halogen radicals.

27. A pharmaceutical composition comprising a therapeutically-effective amount of a compound, said compound selected from the compounds of claim 1; or a pharmaceutically salt or tautomer thereof.

28. A pharmaceutical composition comprising a therapeutically-effective amount of a compound, said compound selected from the compounds of claim 2; or a pharmaceutically salt or tautomer thereof.

29. A pharmaceutical composition comprising a therapeutically-effective amount of a compound, said compound selected from the compounds of claim 3; or a pharmaceutically salt or tautomer thereof.

30. A pharmaceutical composition comprising a therapeutically-effective amount of a compound, said compound selected from the compounds of claim 4; or a pharmaceutically salt or tautomer thereof.

31. A pharmaceutical composition comprising a therapeutically-effective amount of a compound, said compound selected from the compounds of claim 5; or a pharmaceutically salt or tautomer thereof.

32. A pharmaceutical composition comprising a therapeutically-effective amount of a compound, said compound selected from the compounds of claim 21; or a pharmaceutically salt or tautomer thereof.

33. A method of treating a TNF mediated disorder, said method comprising treating the subject having or susceptible to such disorder with a therapeutically-effective amount of a compound of Formula I

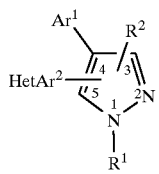

(I)

wherein

R¹ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and R² is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and Ar¹ is aryl unsubstituted or substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr² is pyridinyl, pyrimidinyl or quinolinyl unsubstituted or substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

34. A method of treating a p38 kinase mediated disorder, said method comprising treating the subject having or susceptible to such disorder with a therapeutically-effective amount of a compound of Formula I

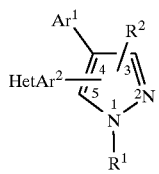

(I)

wherein

R¹ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and R² is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and Ar¹ is aryl unsubstituted or substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr² is pyridinyl, pyrimidinyl or quinolinyl unsubstituted or substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

35. A method of treating inflammation, said method comprising treating the subject having or susceptible to such condition with a therapeutically-effective amount of a compound of Formula I

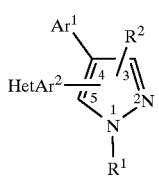

(I)

wherein

R¹ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and R² is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and Ar$^1$ is aryl unsubstituted or substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr$^2$ is pyridinyl, pyrimidinyl or quinolinyl unsubstituted or substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

36. A method of treating arthritis, said method comprising treating the subject having or susceptible to such condition with a therapeutically-effective amount of compound of Formula I

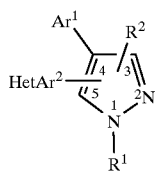

(I)

wherein

R$^1$ is selected from hydrido, alkyl, cycloalkyl, alkenyl, alkynyl, heterocyclyl, cycloalkylalkylene, haloalkyl, hydroxyalkyl, aralkyl, alkoxyalkyl, mercaptoalkyl, alkylthioalkylene, amino, alkylamino, arylamino, aminoalkyl, alkylaminoalkylene, heterocyclylalkylene, aminocarbonylalkylene, and alkylaminocarbonylalkylene; and R$^2$ is selected from hydrido, alkyl, alkenyl, alkynyl, heterocyclyl, haloalkyl, heterocyclylalkyl, amino, alkylamino, aminoalkyl, alkoxy, alkylthio, carboxy, alkoxycarbonyl, carboxyalkyl, aminocarbonylamino, alkylaminocarbonylamino, alkylsulfonyl, aminosulfonyl, alkylsulfonylamino, aminosulfonylamino, alkylaminosulfonylamino, and alkynylamino; wherein the heterocyclyl and heterocyclylalkyl groups are unsubstituted or substituted with one or more radicals independently selected from alkylthio, alkylsulfonyl, alkylsulfinyl, halo, alkyl, alkoxy, aryloxy, aralkoxy, heterocyclyl, haloalkyl, amino, cyano, and hydroxy; and Ar$^1$ is aryl unsubstituted or substituted with one or more radicals independently selected from halo, alkyl, alkenyl, alkynyl, alkoxy, alkenoxy, alkyldioxy, alkylthio, alkylsulfinyl, alkylsulfonyl, amino, aminocarbonyl, cyano, alkoxycarbonyl, formyl, aminosulfonyl, alkylamino, nitro, arylamino, alkylcarbonylamino, halosulfonyl, aminoalkyl, and haloalkyl; and HetAr$^2$ is pyridinyl, pyrimidinyl or quinolinyl unsubstituted or substituted with one or more radicals independently selected from alkylthio, alkylsulfonyl, alkylsulfinyl, halo, alkyl, heterocyclyl, alkoxy, aralkoxy, haloalkyl, amino, cyano, aralkyl, alkylamino, cycloalkylamino, cycloalkenylamino, arylamino, alkynylamino, and aralkylamino; or a pharmaceutically-acceptable salt or a tautomer thereof.

37. The method of claim 33 wherein the TNF mediated disorder is selected from the group of disorders consisting of bone resorption, graft vs. host reaction, atherosclerosis, arthritis, osteoarthritis, rheumatoid arthritis, gout, psoriasis, topical inflammatory disease state, adult respiratory distress syndrome, asthma, chronic pulmonary inflammatory disease, cardiac reperfusion injury, renal reperfusion injury, thrombus, glomerulonephritis, Crohn's disease, ulcerative colitis, inflammatory bowel disease and cachexia.

38. The method of claim 33 wherein the TNF mediated disorder is inflammation.

39. The method of claim 33 wherein the TNF mediated disorder is arthritis.

40. The method of claim 33 wherein the TNF mediated disorder is asthma.

41. The method of claim 33 wherein the compound is selected from the compounds, their tautomers and their pharmaceutically acceptable salts, of the group consisting of
4-(3-methyl-4-phenyl-1H-pyrazol-5-yl)pyridine;
4-(4-fluorophenyl)-5-(4-pyridinyl)-1H-pyrazol-3-amine;
N-[4(4-fluorophenyl)-5-(4-pyridinyl)-1H-pyrazol-3-yl] methanesulfonamide;
N-[4-(4-fluorophenyl)-5-(4-pyridinyl)-1H-pyrazol-3-yl]-N'-methylsulfamide;
[4-(4-fluorophenyl)-5-(4-pyridinyl)-1H-pyrazol-3-yl]urea;
[4-(4-fluorophenyl)-5-(4-pyridinyl)-1H-pyrazol-3-yl] sulfamide;
4-(4-chlorophenyl)-1-methyl-3-(4-pyridinyl)-1H-pyrazol-5-amine;
N-[4-(4-fluorophenyl)-5-(4-pyridinyl)-1H-pyrazol-3-yl]-N'-methylurea;
4-[4-(4-fluorophenyl)-1H-pyrazol-3-yl]pyridine;
4-[4-(4-fluorophenyl)-1-methyl-1H-pyrazol-3-yl]pyridine;
4-(4-fluorophenyl)-3-(4-pyridinyl)-1H-pyrazole-1-ethanol;
4-(4-fluorophenyl)-N,N-dimethyl-3-(4-pyridinyl)-1H-pyrazole-1-ethanamine;
4-[2-[4-(4-fluorophenyl)-3-(4-pyridinyl)-1H-pyrazol-1-yl] ethyl]morpholine;
4-[4-(4-chlorophenyl)-1H-pyrazol-3-yl]pyridine;
1-methyl-4-[2-[4-(4-fluorophenyl)-3-(4-pyridinyl)-1H-pyrazol-1-yl]]piperidine; and
1-methyl-4-[2-[4-(4-fluorophenyl)-5-(4-pyridinyl)-1H-pyrazol-1-yl]piperidine.

42. The method of claim 34 wherein the disorder is a p38α kinase mediated disorder.

43. The method of claim 34 wherein the P38 kinase mediated disorder is selected from the group of disorders consisting of bone resorption, graft vs. host reaction, atherosclerosis, arthritis, osteoarthritis, rheumatoid arthritis, gout, psoriasis, topical inflammatory disease state, adult respiratory distress syndrome, asthma, chronic pulmonary inflammatory disease, cardiac reperfusion injury, renal reperfusion injury, thrombus, glomerulonephritis, Crohn's disease, ulcerative colitis, inflammatory bowel disease and cachexia.

44. The method of claim 34 wherein the p38 kinase mediated disorder is inflammation.

45. The method of claim 34 wherein the p38 kinase mediated disorder is arthritis.

46. The method of claim 34 wherein the p38 kinase mediated disorder is asthma.

47. The method of claim 34 wherein the compound is selected from the compounds, their tautomers and their pharmaceutically acceptable salts, of the group consisting of 4-(3-methyl-4-phenyl-1H-pyrazol-5-yl)pyridine;
4-(4-fluorophenyl)-5-(4-pyridinyl)-1H-pyrazol-3-amine;
N-[4(4-fluorophenyl)-5-(4-pyridinyl)-1H-pyrazol-3-yl]methanesulfonamide;
N-[4-(4-fluorophenyl)-5-(4-pyridinyl)-1H-pyrazol-3-yl]-N'-methylsulfamide;
[4-(4-fluorophenyl)-5-(4-pyridinyl)-1H-pyrazol-3-yl]urea;
[4-(4-fluorophenyl)-5-(4-pyridinyl)-1H-pyrazol-3-yl]sulfamide;
4-(4-chlorophenyl)-1-methyl-3-(4-pyridinyl)-1H-pyrazol-5-amine;
N-[4-(4-fluorophenyl)-5-(4-pyridinyl)-1H-pyrazol-3-yl]-N'-methylurea;
4-[4-(4-fluorophenyl)-1H-pyrazol-3-yl]pyridine;
4-[4-(4-fluorophenyl)-1-methyl-1H-pyrazol-3-yl]pyridine;
4-(4-fluorophenyl)-3-(4-pyridinyl)-1H-pyrazole-1-ethanol;
4-(4-fluorophenyl)-N,N-dimethyl-3-(4-pyridinyl)-1H-pyrazole-1-ethanamine;
4-[2-[4-(4-fluorophenyl)-3-(4-pyridinyl)-1H-pyrazol-1-yl]ethyl]morpholine;
4-[4-(4-chlorophenyl)-1H-pyrazol-3-yl]pyridine;
1-methyl-4-[2-[4-(4-fluorophenyl)-3-(4-pyridinyl)-1H-pyrazol-1-yl]]piperidine; and
1-methyl-4-[2-[4-(4-fluorophenyl)-5-(4-pyridinyl)-1H-pyrazol-1-yl]piperidine.

48. A compound of claim 1 that is 4-[4-(4-fluorophenyl)-1H-pyrazol-3-yl]pyridine or a pharmaceutically-acceptable salt or a tautomer thereof.

49. The method of claim 33 wherein the compound is 4-[4-(4-fluorophenyl)-1H-pyrazol-3-yl]pyridine or a pharmaceutically-acceptable salt or a tautomer thereof.

50. The method of claim 34 wherein the compound is 4-[4-(4-fluorophenyl)-1H-pyrazol-3-yl]pyridine or a pharmaceutically-acceptable salt or a tautomer thereof.

* * * * *